US009598687B2

(12) United States Patent
Hunter et al.

(10) Patent No.: US 9,598,687 B2
(45) Date of Patent: Mar. 21, 2017

(54) METHODS FOR PROCESSING COAGULATION FACTORS

(75) Inventors: Alan Hunter, Gaithersburg, MD (US); Xiangyang Wang, Gaithersburg, MD (US); Timothy Pabst, Gaithersburg, MD (US); Michaela Wendeler, Gaithersburg, MD (US); Jihong Wang, Gaithersburg, MD (US); Kendall Carey, Gaithersburg, MD (US); Robert Strouse, Gaithersburg, MD (US); Johnson Varghese, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 286 days.

(21) Appl. No.: 14/342,017

(22) PCT Filed: Aug. 31, 2012

(86) PCT No.: PCT/US2012/053319
§ 371 (c)(1),
(2), (4) Date: Jun. 2, 2014

(87) PCT Pub. No.: WO2013/036445
PCT Pub. Date: Mar. 14, 2013

(65) Prior Publication Data
US 2014/0303353 A1    Oct. 9, 2014

Related U.S. Application Data

(60) Provisional application No. 61/531,314, filed on Sep. 6, 2011.

(51) Int. Cl.
| | |
|---|---|
| *A61K 38/36* | (2006.01) |
| *C07K 14/745* | (2006.01) |
| *C07K 1/18* | (2006.01) |
| *C07K 1/20* | (2006.01) |
| *C07K 1/34* | (2006.01) |
| *C07K 1/36* | (2006.01) |
| *C12N 9/74* | (2006.01) |
| *C12N 9/64* | (2006.01) |

(52) U.S. Cl.
CPC .......... *C12N 9/6429* (2013.01); *C07K 14/745* (2013.01); *C12N 9/647* (2013.01)

(58) Field of Classification Search
CPC ..... C12N 9/6429; C12N 9/647; C07K 14/745
See application file for complete search history.

(56) References Cited

U.S. PATENT DOCUMENTS

| | | | |
|---|---|---|---|
| 5,092,992 | A | 3/1992 | Crane |
| 5,589,571 | A | 12/1996 | King |
| 2010/0081187 | A1 | 4/2010 | Griffith et al. |
| 2010/0159512 | A1 | 6/2010 | Osther |

FOREIGN PATENT DOCUMENTS

| | | |
|---|---|---|
| EP | 0363126 A2 | 4/1990 |
| WO | 8803926 A1 | 6/1988 |
| WO | 9640883 A1 | 12/1996 |
| WO | 9837086 A1 | 8/1998 |
| WO | 2005038019 A1 | 4/2005 |

OTHER PUBLICATIONS

Dichtelmuller, H.O., et al. 2009 Transfusion 49: 1931-1943.*
Josic, D., et al. 2003 Journal of Chromatography B 790: 183-197.*
Sun et al., "Vitamin K epoxide reductase significantly improves carboxylation in a cell line overexpressing factor X", Blood, 106(12):3811-3813 (2005).
Extended European Search Report issued in EP 12830128.0 on Jul. 10, 2015 (9 pages).
Fischer et al, "Purification of Recombinant Human Coagulation Factors II and IX Andprotein S Expressed in Recombinant Vaccinia Virus-Infected Vero Cells", Journal of Biotechnology, vol. 38, No. 2, Jan. 1, 1995 (Jan. 1, 1995), pp. 129-136.
Husi et al: "Separation of Human Vitamin Kdependent Coagulation Proteins Using Hydrophobic Interaction Chromatography", Journal of Chromatography, Biomedical Applications, vol. 736, No. 1-2, Dec. 24, 1999 (Dec. 24, 1999), pp. 77-88.
International Search Report issued in PCT/US2012/053319 by ISA/US on Jan. 17, 2013 (3 pages).
Wendeler et al., "Process-scale purification and analytical characterization of highly gamma-carboxylated recombinant human prothrombin", Journal of Chromatography, vol. 1325, Dec. 15, 2013 (Dec. 15, 2013), pp. 171-178.

* cited by examiner

*Primary Examiner* — Marsha Tsay
(74) *Attorney, Agent, or Firm* — Melissa Pytel

(57) ABSTRACT

The present application relates to methods for purifying recombinant coagulation factor proteins, including for example, prothrombin (Factor II). In embodiments, the methods provide purified prothrombin that exhibit increased bioactivity and reduced levels of thrombin, thereby increasing the safety of the prothrombin. Also provided are purified recombinant coagulation factor proteins.

28 Claims, 6 Drawing Sheets

Missing Gla (X/10)

METHODS FOR PROCESSING COAGULATION FACTORS

CROSS-REFERENCE TO RELATED APPLICATIONS

This application is a U.S. National Stage application of International Application No. PCT/US2012/053319, filed on Aug. 31, 2012, said International Application No. PCT/US2012/053319 claims benefit under 35 U.S.C. §119(e) of U.S. Provisional Application No. 61/531,314, filed Sep. 6, 2011. The above listed application is incorporated by reference herein in its entirety for all purposes.

REFERENCE TO THE SEQUENCE LISTING

This application incorporates by reference a Sequence Listing submitted with this application as text file entitled 2012-09-14_Sequence.txt, created on Sep. 14, 2012, and having a size of 6.57 kilobytes.

BACKGROUND OF THE INVENTION

Field of the Invention

The present application relates to methods for purifying recombinant coagulation factor proteins, including for example, prothrombin (Factor II). In embodiments, the methods provide purified prothrombin that exhibit increased bioactivity and reduced levels of thrombin, thereby increasing the safety of the prothrombin. Also provided are purified recombinant coagulation factor proteins.

Background of the Invention

Coagulation factors for therapeutic use (e.g., for the treatment of hemophilia and other blood disorders) can be obtained from human plasma, though purification can be complex. Even with extensive safety measures and testing of blood-derived protein products, contamination with infectious viruses or prions cannot be ruled out. Therefore, is highly desirable to produce human therapeutic proteins from recombinant cells grown in media without animal derived components. This is not always straightforward as many proteins require a mammalian host to be produced in a fully functional form, i.e. to be correctly post-translationally modified.

Factor II (prothrombin) is a coagulation factor necessary for blood clotting. In the extrinsic (or tissue factor) blood coagulation pathway, tissue factor triggers a coagulation cascade in which prothrombin, in the presence of Factor Xa, FactorVa, phospholipids, and $Ca^{2+}$ ions, becomes the activated form, Factor IIa (thrombin). Thrombin acts through multiple pathways to stop bleeding by converting fibrinogen to fibrin clots, and participating in other pro-coagulation pathways.

During the production and purification of recombinant prothrombin protein, thrombin can be present as a product-related, impurity. Levels of free thrombin generally must be kept at low levels to increase product safety. In addition, recombinant prothrombin contains 10 gamma-carboxyglutamic acid "Gla-residues" in the N-terminal domain. These residues are thought to chelate $Ca^{2+}$ ions, which mediates the protein's binding to phospholipid membranes, a prerequisite for prothrombin activation to thrombin.

The inventors of the present application have identified a need for purification methods that provide recombinant purified prothrombin having high levels of γ-carboxylated glutamic acid residues and low thrombin contamination.

SUMMARY OF PREFERRED EMBODIMENTS

The present application provides methods of purification of coagulation proteins to meet the needs identified above.

In embodiments, methods are provided for purifying a recombinant coagulation factor protein. The methods suitably comprise providing a mixture comprising the recombinant coagulation factor protein. The mixture is filtered through at least a first column to produce a first column product. The first column product is filtered through a poly(ethyleneimine) (PEI) column to produce a PEI column product, and the purified recombinant coagulation factor protein is recovered. Suitably, the purified recombinant coagulation factor protein comprises less than about 0.5/10 missing γ-carboxylated glutamic acid sites. In embodiments, the recombinant coagulation factor protein is prothrombin (Factor II).

Suitably, the mixture is a filtered mixture from a bioreactor. In exemplary embodiments, the filtering of the mixture comprises filtering through a first anion exchange column, suitably a binding and elution filtering. In embodiments, the first column product can be filtered through a second anion exchange column, suitably a flowthrough filtering.

In embodiments, the first column is inactivated product with a solvent/detergent inactivation before filtering through the poly(ethyleneimine) column. In embodiments, the filtering through the poly(ethyleneimine) column is a binding and elution filtering. Suitably, the PEI column product is filtered through hydrophobic interaction column (HIC), for example in a binding and elution filtering. In embodiments, the methods can comprise nanofiltering prior to the recovery.

In suitable embodiments, the recombinant prothrombin protein is substantially free of thrombin, and comprises less than about 0.8/10, 0.7/10, 0.6/10, 0.5/10 or 0.4/10 missing γ-carboxylated glutamic acid sites.

In further embodiments, methods are provided method for purifying a recombinant coagulation factor protein (e.g., prothrombin (Factor II)). The methods suitably comprise providing a mixture comprising the recombinant coagulation factor protein and filtering the mixture through at least a first anion exchange column (e.g., a binding and elution filtering) to produce a first anion exchange column product. The first anion exchange column product is inactivated with a solvent/detergent viral inactivation to produce an inactivated mixture. Suitably, the inactivated mixture is filtered through a poly(ethyleneimine) (PEI) column (e.g., a binding and elution filtering) to produce a PEI column product, and the PEI column product is filtered through a hydrophobic interaction column (HIC) to produce a HIC product. In embodiments, the HIC product is then filtered (e.g., a nanofiltering) and the purified recombinant coagulation factor protein is recovered. In embodiments, the purified recombinant coagulation factor protein comprises less than about 0.8/10, 0.7/10, 0.6/10, 0.5/10 or 0.4/10 missing γ-carboxylated glutamic acid sites. In certain embodiments, prior to filtering through a PEI column, the first anion exchange column product is filtered through a second anion exchange column (e.g., a flowthrough filtering) to produce a second anion exchange column product. The second anion exchange column product is then filtered through a PEI column to produce a PEI column product.

Suitably, the recombinant prothrombin protein is substantially free of thrombin, and suitably comprises less than about 0.8/10, 0.7/10, 0.6/10, 0.5/10 or 0.4/10 missing γ-carboxylated glutamic acid sites.

In further embodiments, methods are provided for purifying a recombinant prothrombin (Factor II) protein. The methods suitably comprise providing a filtered mixture from a bioreactor comprising the recombinant prothrombin protein, binding and elution filtering the mixture through a first anion exchange column to produce a first anion exchange column product, flowthrough tittering the first anion exchange column product through a second anion exchange column to produce a second anion exchange column product, inactivating the second anion exchange column product with a solvent/detergent viral inactivation to produce an inactivated mixture, binding and elution filtering the inactivated mixture through a poly(ethyleneimine) (PEI) column to produce a PEI column product, binding and elution filtering the PEI column product through a hydrophobic interaction column (HIC) to produce a HIC product, nanofiltering the HIC product and recovering the purified recombinant prothrombin protein.

Suitably, the purified recombinant prothrombin protein Factor II) comprises less than about 0.8/10, 0.7/10, 0.6/10, 0.5/10 or 0.4/10 γ-carboxylated glutamic acid sites and is substantially free of thrombin.

In further embodiments, purified recombinant prothrombin proteins (Factor II) are provided. Suitably, the proteins comprise less than about 0.8/1.0, 0.7/10, 0.6/10, 0.5/10 or 0.4/10 missing γ-carboxylated glutamic acid sites and are substantially free of thrombin.

In embodiments, the purified recombinant prothrombin exhibits greater than about 70% bioactivity in a clotting assay and/or greater than about 70% bioactivity in a calibrated automated thrombogram (CAT) assay. Suitably, the protein comprises less than about 2 ng/ml thrombin.

Further embodiments, features, and advantages of the embodiments, as well as the structure and operation of the various embodiments, are described in detail below with reference to accompanying drawings.

DETAILED DESCRIPTION OF PREFERRED EMBODIMENTS

Figure 1:
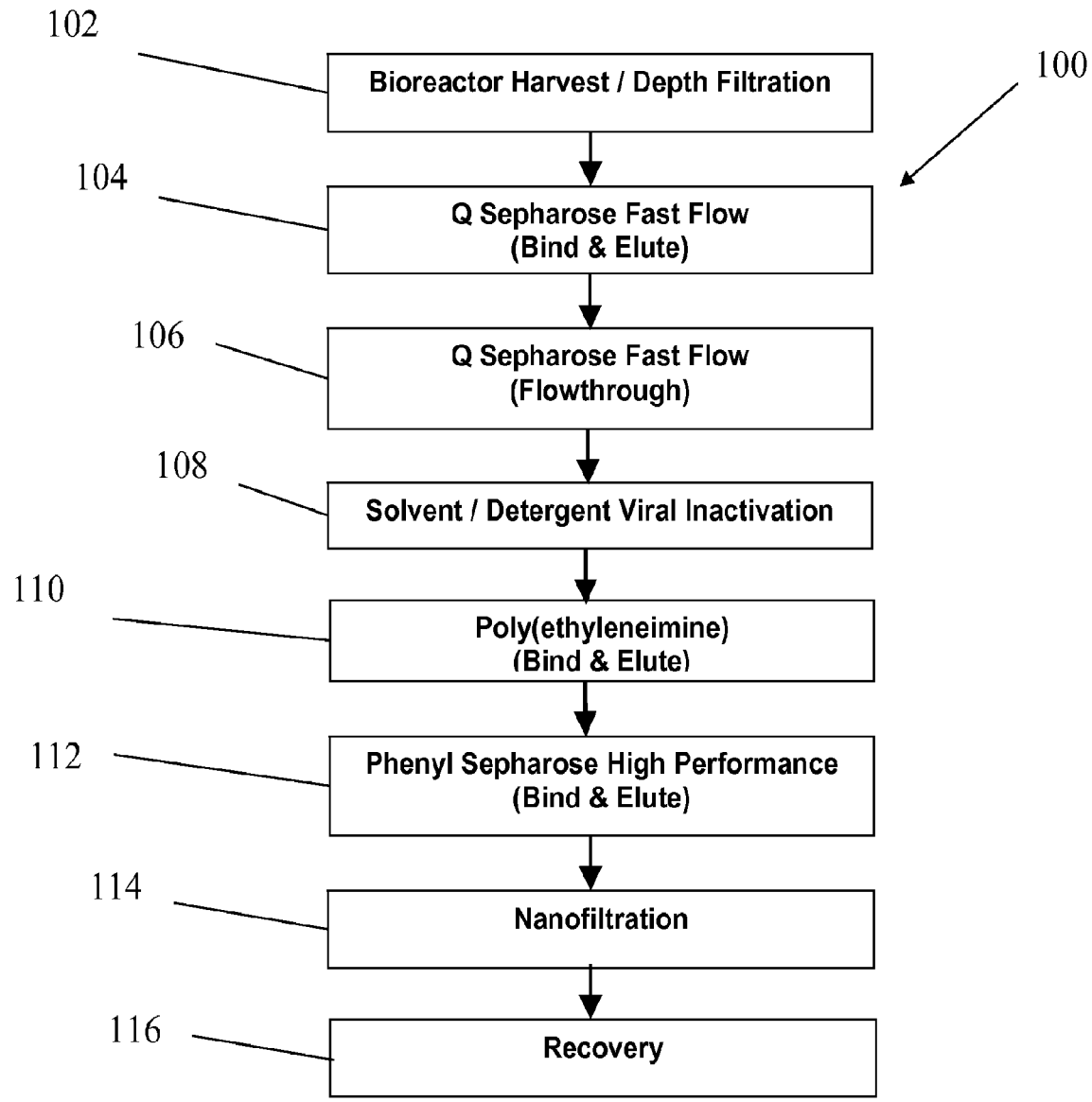
FIG. 1 shows a flowchart of an exemplary method of purification disclosed herein.

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present application pertains, unless otherwise defined. Reference is made herein to various methodologies and materials known to those of skill in the art. Standard reference works setting forth the general principles of recombinant DNA technology include Sambrook et al., "Molecular Cloning: A Laboratory Manual," 2nd Ed., Cold Spring Harbor Laboratory Press, New York (1989); Kaufman et al. Eds., "Handbook of Molecular and Cellular Methods in Biology in Medicine," CRC Press, Boca Raton (1995); and McPherson, Ed., "Directed Mutagenesis: A Practical Approach," IRL Press, Oxford (1991), the disclosures of each of which are incorporated by reference herein in their entireties.

In embodiments, methods are provided for purifying a recombinant coagulation factor protein. In suitable embodiments, the methods comprise providing a mixture comprising the recombinant coagulation factor protein. The mixture is filtered through at least a first column to produce a first column product. The first column product is then filtered through a poly(ethyleneimine) (PEI) column to produce a PEI column product. The purified recombinant coagulation factor protein is then recovered from the PEI column product.

In exemplary embodiments, the recombinant coagulation factor protein that is purified is human prothrombin (Factor II). The terms "prothrombin," "Factor II," "recombinant prothrombin" and "recombinant Factor II" are used interchangeably throughout. Other recombinant coagulation factor proteins can be purified using the methods described herein and include, for example, Factor VI and Factor IX.

As used herein, "recombinant coagulation factor protein(s)" refers to coagulation factor peptide, polypeptide or protein produced using any suitable expression system, including both prokaryotic and eukaryotic expression systems, or using phage display methods (see, e.g., Dower et al., WO 91/17271 and McCafferty et al., WO 9201047; and U.S. Pat. No. 5,969,108, which are herein incorporated by reference in their entirety). It should be understood that the term "protein" and proteins" are utilized interchangeably throughout.

As used herein the term "peptide" or "polypeptide" refers to a polymer formed from the linking, in a defined order, of preferably, α-amino acids, D-, L-amino acids, and combinations thereof. The link between one amino acid residue and the next is referred to as an amide bond or a peptide bond. Proteins are polypeptide molecules having multiple polypeptide subunits. The distinction is that peptides are generally short and polypeptides/proteins are generally longer amino acid chains. The term "protein" is intended to also encompass derivatized molecules such as glycoproteins and lipoproteins as well as lower molecular weight polypeptides. "Amino acid sequence" and like terms, such as "polypeptide" or "protein", are not meant to limit the indicated amino acid sequence to the complete, native amino acid sequence associated with the recited protein molecule.

Methods of producing recombinant coagulation factor proteins using various host cells such as bacteria, plant, yeast, insect and mammalian cells are well known. For example, numerous expression systems are available for expression of proteins utilizing *Escherichia coli* (*E. coli*), other bacterial hosts, yeast, and various higher eukaryotic cells such as, for example, COS, CHO, HeLa and myeloma cell lines.

Briefly, the expression of natural or synthetic nucleic acids encoding the desired coagulation factor protein(s) is generally achieved by operably linking the DNA or cDNA to a promoter (which is either constitutive or inducible), followed by incorporation into an expression cassette. The cassettes can be suitable for replication and integration in either prokaryotic or eukaryotic cell lines. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli*, this includes a promoter such as the T7, trp, lac, or lambda promoters, a ribosome binding site and a transcription termination signal. For eukaryotic cells, the control sequences can include a promoter and an enhancer derived from immunoglobulin genes, SV40, cytomegalovirus, and a polyadenylation sequence, and may include splice donor and acceptor sequences. The cassettes can be transferred into the chosen host cell by well-known methods such as calcium chloride transformation or electroporation for *E. coli* and calcium phosphate treatment, or electroporation or lipofection for mammalian cells. Cells transformed by the cassettes can be selected by resistance to antibiotics conferred by genes contained in the cassettes, such as the amp, gpt, neo and hyg genes.

In embodiments, the recombinant coagulation factor protein is human prothrombin (Factor II) produced, for example, as in U.S. Pat. Nos. 7,842,477 and 7,989,193, the disclosures of each of which are incorporated by reference herein in there entireties, U.S. Pat. Nos. 7,842,477 and 7,989,193 disclose nucleic acid sequences, plasmids and host cells useful in producing the recombinant prothrombin.

An exemplary purification method is shown in FIG. 1 and described in further detail herein.

As used throughout, the terms "purify," "purification" or "purified" are used to refer to a process by which the desired recombinant protein or proteins are removed from other proteins or undesired products or structures (or the undesired products or structures are removed from the desired proteins) such that the desired protein or proteins are at least about 75% free of other proteins, products or structures, at least about 80% free of other proteins, products or structures, at least about 90% free of other proteins, products or structures, more suitably at least about 95% free of other proteins, products or structures, and most suitably at least about 98% of other proteins, products or structures.

The purification methods described throughout suitably remove structures such as unwanted host cell proteins (HCP) and other structures (e.g., DNA, RNA), as well as unwanted, undesirable or non-optimal forms of the recombinant coagulation factor protein, from the final, desired recombinant protein or proteins.

As used herein, the term "filtering" is used to mean that a mixture comprising the recombinant protein(s) is placed in contact with a filtration medium, so that undesired or unwanted components in the solution or mixture are removed by the filtration medium. A "mixture" comprising the recombinant protein may often also include various HCPs, nucleic acids, other proteins, including recombinant forms of the protein, etc., in a buffer or other liquid medium.

In embodiments, the mixtures of the recombinant coagulation factor proteins are the product of a filtered mixture from a bioreactor, or can be the direct product of a bioreactor, or other method that is used to produce the recombinant coagulation factor protein.

Exemplary filtration media for use in the methods disclosed herein include various paper filters, woven fibers, polymer-based column filtration media, agarose, dextran and natural filtration media, as well as other media known in the art. Suitably, the filtration media are polymer-based filtration media, as well as agarose or dextran-based media, including for example, SEPHAROSE™, SEPHADEX™ and poly (ethyleneimine) filtration media.

In exemplary embodiments, the mixture comprising a recombinant coagulation factor is filtered through a first anion exchange column (i.e, a chromatography or filtration column that has been prepared using an agarose filtration media). Examples of suitable anion exchange columns include Q SEPHAROSE™ columns, such as Q SEPHAROSE™ Fast Flow columns, which comprise highly cross-linked 4% agarose, spherical beads, having a bead size in the range of about 45-165 µm. (GE Healthcare, Piscataway, N.J.). Methods of preparing such columns, including amounts of the media to utilize, apparatus for holding and preparing the columns, as well as methods for filtering mixtures utilizing these columns are well known to those of ordinary skill in the art. Such methods suitably include the addition of a pre-determined volume of the mixture to a column, the addition of a buffer or other media to equilibrate or wash the column, and passing a buffer or wash media through the column at a pre-determined flow rate.

In embodiments, the mixture is filtered through a first anion exchange column, followed by a second anion exchange column. Suitably, the first and second anion exchange columns that are utilized are Q SEPHAROSE™ Fast Flow columns. In embodiments, additional anion exchange columns can also be utilized. For example, the mixture can be filtered through two, three, four, five, six, seven, eight, nine, ten, etc., anion exchange columns. Additional types of columns or filtration media can also be used to initially filter the mixture comprising recombinant coagulation factor proteins.

The resulting product of filtration is referred to herein as a "product" "column product," "anion exchange column product" or "PEI column product," depending on the type of column that is used for the filtration. Filtration through the anion exchange column(s) can be either a flowthrough filtration or a binding and elution filtration. As used herein, "flowthrough" filtration refers to filtration in which a mixture is added to a column, suitably followed by a buffer or wash solution, and then the mixture is passed through the column. The resulting product of the filtration ("a column product") is the material that passes through the column as unbound product. Any unwanted or undesirable components (e.g., DNA, proteins, cell products, etc.), are retained on the column.

As used herein "binding and elution" filtration or filtering, or "bind and elute" refers to filtration with a column where the mixture is added to a column, and suitably followed by a wash or equilibration buffer. The desired material is initially retained on the column (i.e., binds to or is retained by the column media), while unwanted or undesirable components pass through the column. The desired product is then eluted from the column (i.e., product originally bound to the column) by elution with a suitable buffer. In such embodiments, the column product is the material that is recovered after the removal of the unwanted or undesired components of the mixture that passed through the column and were not retained.

In exemplary embodiments, filtering of the mixture through the first anion exchange column (e.g., a SEPHAROSE™ column) comprises a binding and elution filtering to produce an anion exchange column product. Suitably, if a second anion exchange column is used to filter the mixture, filtering through the second anion exchange (e.g., SEPHAROSE™) column comprises flowthrough filtering. Any additional filtrations through anion exchange columns can comprise binding and elution filtering or flowthrough filtering, as desired.

In embodiments, the methods further comprise inactivating the first column product (i.e., the product of the first anion exchange column or the product of the second anion exchange column in cases where two anion exchange columns are utilized) with a solvent/detergent inactivation to generate an inactivated mixture. Suitably this inactivation occurs prior to any further filtration, e.g., with a poly(ethyleneimine) column. Suitably, the inactivating comprises use of a detergent to interrupt the interactions between the molecules in a virus's lipid coating. Suitably a solvent is used that creates an environment in which the aggregation reaction between the lipid coat and the detergent occur quickly. Exemplary detergents and solvents are known in the art, and include for example, the detergent Triton-X 100.

Suitably, the inactive mixture is filtered through at least one poly(ethyleneimine) (PEI) column to produce a PEI column product. In suitable embodiments, filtering of the inactivated mixture through a poly(ethyleneimine) column comprises a binding and elution filtering.

Examples of poly(ethyleneimine) columns for use in the methods described herein include a BAKERBOND™ XWP 500 Poly PEI-35 (poly(ethyleneimine)) column (PolyPEI). Such exemplary columns comprise poly(ethyleneimine) (PEI) bonded on a hydrophobic polymer (AVANTOR™, Phillipsburg, N.J.).

In embodiments, the methods further comprise filtering the PEI column product through one or more anion exchange columns, suitably a Phenyl SEPHAROSE™ High Performance column. In embodiments, the filtration of the PEI column product through the hydrophobic interaction column comprises a binding and elution filtering. Other column filtrations following the PEI filtration can also be used to further purify the recombinant coagulation factor protein prior to recovery.

In suitable embodiments, prior to the recovery of the purified recombinant coagulation protein, the mixture is nanofiltered. In embodiments, nanofiltering can occur after filtration through the PEI column (i.e., the PEI column product is nanofiltered), and in other embodiments, the nanofiltering can occur following the filtering of the PEI column product through a hydrophobic interaction column (HIC) the HIC product is nanofiltered) or other suitable columns. Exemplary methods for nanofiltering and filtration media for nanofiltration are well known in the art, and suitably utilize membranes having a pore size on the order of about 1 nm. Nanofiltration membranes suitably have a molecular weight cut-off (MWCO) less than 1000 atomic mass units (daltons).

The methods described herein suitably produce a recombinant coagulation protein, suitably prothrombin (Factor II), that is substantially free of thrombin. As described herein, removal of thrombin from the recombinant prothrombin (or reduction of the amount of thrombin present to suitable levels) increases the safety of the final protein product. As used herein, substantially free of thrombin is used to indicate that the final product comprises less than about 20% thrombin, suitably less than about 15%, less than about 10%, less than about 5%, less than about 1%, less than about 0.5%, less than about 0.1%, less than about 0.05%, less than about 0.01%, less than about 0.005% or less than about 0.001% thrombin, based on total mass of the protein product. Suitably, the amount of thrombin in the final product is less than about 10 ng/ml thrombin, more suitably less than about 9 ng/ml thrombin, less than about 8 ng/ml thrombin, less than about 7 ng/ml thrombin, less than about 6 ng/ml thrombin, less than about 5 ng/ml thrombin, less than about 4 ng/ml thrombin, less than about 3 ng/ml thrombin, less than about 2 ng/ml thrombin, or less than about 1 ng/ml thrombin.

One of the major obstacles in obtaining large amounts of fully functional recombinant human coagulation factors lies in the Gla-domain present in Factor II, Factor VII, Factor IX, Factor X and Protein C. This domain contains glutamic acid residues that are post-translationally modified by addition of carboxyl groups. The production of these factors are hampered by the fact that over-expression of them result in under-carboxylated, and hence inactive, protein. The Gla modifications are a result of the action of a vitamin K-dependent enzyme called γ-glutamyl carboxylase (GGCX) (see e.g., WO 88/03926; Wu et al. *Science* 254(5038): 1634-1636, 1991).

Figure 2:
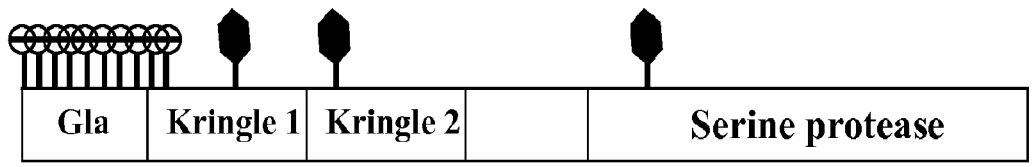
FIG. 2 shows the domain architecture of prothrombin, showing the 10 γ-carboxylated glutamic (Gla) acid residues in the N-terminal Gla-domain

As shown in FIG. 2, recombinant prothrombin contains 10 "Gla-residues" in the N-terminal domain. These are γ-carboxylated glutamic acid (Gla) residues that impacts the biological activity of the protein. These residues are thought to chelate $Ca^{2+}$ ions, which mediate the protein's binding to phospholipid membranes, a prerequisite fir prothrombin activation to thrombin.

For human Factor II (prothrombin), at least 8 out of 10 Glu residues have to be correctly modified in order to obtain fully functional prothrombin (Malhotra, et al., *J. Biol. Chem.* 260: 279-287, 1985; Seegers and Walz 'Prothrombin and other vitamin K proteins', CRC Press, 1986). Extensive efforts to obtain high production levels of rhFII have been made using several different systems such as CHO cells, BHK cells, 293 cells and vaccinia virus expression systems, (Jorgensen et al., *J. Biol. Chem.* 262: 6729-6734, 1987; Russo et al., *Biotechnol Appl Biochem* 14(2): 222-233, 1991; Fischer et al., *J Biotechnol* 38(2): 129-136, 1995; Herlitschka et al. *Protein Expr. Purif.* 8(3): 358-364, 1996; Russo et al., *Protein Expr. Purif.* 10: 214-225, 1997). Exemplary methods for production recombinant Factor II are disclosed, for example, in U.S. Pat. Nos. 7,842,477 and 7,989,193, the disclosures of which are incorporated by reference herein in their entireties.

The recombinant coagulation factor proteins (suitably prothrombin (Factor II)) purified according to the methods described herein suitably comprise less than about 1 out of 10 (1/10) missing γ-carboxylated glutamic acid (Gla) sites. That is, of the 10 glutamic acid sites in the protein, when considering the average over a total protein sample, suitably less than 1/10 of the Gla sites are not γ-carboxylated, i.e., on average, less than 1/10 γ-carboxylated glutamic acid (Gla) sites are missing. In embodiments, the methods described herein suitably provide prothrombin comprising less than about 0.9/10 missing γ-carboxylated glutamic acid sites, more suitably less than about 0.8/10 missing γ-carboxylated glutamic acid sites, less than about 0.7/10 missing γ-carboxylated glutamic acid sites, less than about 0.6/10 missing γ-carboxylated glutamic acid sites, less than about 0.5/10 missing γ-carboxylated glutamic acid sites, less than about 0.4/10 missing γ-carboxylated glutamic acid sites, less than about 0.3/10 missing γ-carboxylated glutamic acid sites, less than about 0.2/10 missing γ-carboxylated glutamic acid sites, less than about 0.2/10 missing γ-carboxylated glutamic acid sites, or no missing γ-carboxylated glutamic acid sites, over the average of a sample.

As described herein, the inventors have discovered that the disclosed methods produce purified recombinant coagulation factor proteins, including for example, prothrombin (Factor II) that are substantially free of thrombin and that also have less than about 0.5/10 missing γ-carboxylated glutamic acid sites. Testing the bioactivity of these purified recombinant coagulation proteins demonstrates that the reduction in the number of missing γ-carboxylated glutamic acid sites correlates with an increase in bioactivity as measured in Clot and CAT assays (see description in Examples of Clot and CAT bioactivity assays). See FIG. 3. As described in the Examples, this correlation provides bioactivities of the purified proteins that are greater than about 70%, suitably greater than about 75%, greater than about 80%, greater than about 85%, greater than about 90%, greater than about 95%, or about 100% bioactive, when compared to a reference standard that demonstrates 100% bioactivity measurable by the assays.

While not wishing to be bound by any theory as to the reason for the increase in the activity, it is believed that purification of the recombinant coagulation protein by filtration through a poly(PEI) column provides recombinant coagulation factor proteins that comprise reduced numbers of missing γ-carboxylated glutamic acid sites (i.e., less than 0.5 missing γ-carboxylated glutamic acid sites).

In further embodiments, additional methods are provided for purifying a recombinant coagulation factor. Suitably, the methods comprise providing a mixture comprising the recombinant coagulation factor protein. The mixture is filtered through at least a first anion exchange column to produce a first anion exchange column product. The first anion exchange column product is inactivated with a solvent/detergent viral inactivation to produce an inactivated mixture. The inactivated mixture is filtered through a poly(ethyleneimine) (PEI) column to produce a PEI column product. The PEI column product is filtered through a hydrophobic interaction column (HIC) to produce a HIC product. The HIC product is further filtered. The purified recombinant coagulation factor protein is then recovered.

Suitably, the recombinant coagulation factor protein is prothrombin (Factor II), though the methods can be readily extended to other recombinant coagulation factor proteins.

In exemplary embodiments, the initial mixture comprising a recombinant coagulation factor protein is a filtered mixture from a bioreactor.

In embodiments, the filtering through at least a first anion exchange column comprises a binding and elution filtering, and can further comprise filtering the first anion exchange column product through a second anion exchange column. Additional anion exchange columns can also be utilized. Suitably, the filtering through a second anion exchange column comprises a flowthrough filtering.

In exemplary embodiments, the filtering of the anion exchange column product through the PEI filter comprises a binding and elution filtering. Further filtering of the PEI column product also suitably comprises a hydrophobic interaction column (HIC). In embodiments, filtering of the HIC product comprises nanofiltering.

The methods described herein can also comprise additional filtration following recovery of the recombinant Factor II, including for example, ultrafiltration or diafiltration of the final product.

As described throughout, the purification methods suitably produce recombinant prothrombin protein products that are substantially free of thrombin. In addition, the recombinant coagulation factor protein suitably comprises less than about 1/10 missing γ-carboxylated glutamic acid sites, more suitably less than about 0.9/10 missing γ-carboxylated glutamic acid sites, less than about 0.8/10 missing γ-carboxylated glutamic acid sites, less than about 0.7/10 missing γ-carboxylated glutamic acid sites, less than about 0.6/10 missing γ-carboxylated glutamic acid sites, less than about 0.5/10 missing γ-carboxylated glutamic acid sites, less than about 0.4/10 missing γ-carboxylated glutamic acid sites, less than about 0.3/10 missing γ-carboxylated glutamic acid sites, less than about 0.2/10 missing γ-carboxylated glutamic acid sites, less than about 0.2/10 missing γ-carboxylated glutamic acid sites, or no missing γ-carboxylated glutamic acid sites.

In further embodiments, additional methods for purifying a recombinant prothrombin (Factor II) protein are provided. FIG. 1 shows flowchart 100 of an exemplary method. Suitably, a filtered mixture from a bioreactor comprising the recombinant prothrombin protein is provided 102. In embodiments, this mixture can be the product of a depth filtration of a bioreactor harvest.

The mixture is the filtered 104 through a first anion exchange column (suitably a Q SEPHAROSE™ Fast Flow column), using binding and elution filtration, to produce a first anion exchange column product. The first anion exchange column product is filtered 106 through a second anion exchange column (suitably a Q SEPHAROSE™ Fast Flow column), suitably using flowthrough filtration to produce a second anion exchange column product. In 108, second anion exchange column product is inactivated with a solvent/detergent viral inactivation to produce an inactivated mixture.

The inactivated mixture is then filtered 110 through a poly(ethyleneimine) (PET) column, suitably using binding and elution filtration, to produce a PEI column product. The PEI column product is then filtered 112 through a hydrophobic interaction column (for example a phenyl SEPHAROSE™ High Performance column), suitably using binding and elution filtration, to produce a HIC product. The HIC product is then nanofiltered 114, and the purified recombinant prothrombin protein is recovered 116.

As described herein, suitably, the purified recombinant prothrombin protein is substantially free of thrombin and comprises less than about 0.5/10 missing γ-carboxylated glutamic acid sites, more suitably less than about 0.4/10 missing γ-carboxylated glutamic acid sites.

In embodiments, the methods described herein consist of the recited steps, such that no additional intervening steps beyond those recited are allowed. In further embodiments, the methods described herein consist essentially of the recited steps. In such embodiments, the addition of steps that alter the physical or chemical nature of the recombinant protein are considered a material alteration to such methods and are thus excluded from such methods that consist essentially of the recited steps.

It should be understood that the order and number of filtrations in the methods described herein can be modified while still achieving the desired, purified recombinant coagulation factor protein having the desired bioactivity, low levels of thrombin, and reduced levels of missing γ-carboxylated glutamic acid sites.

In further embodiments, a purified recombinant prothrombin protein (Factor II) is provided. Suitably, the purified recombinant Factor II protein comprises less than about 1/10 missing γ-carboxylated glutamic acid sites and is substantially free of thrombin.

Suitably, the purified recombinant Factor II protein comprises less than about 0.9/10 missing γ-carboxylated glutamic acid sites, more suitably less than about 0.8/10 missing γ-carboxylated glutamic acid sites, less than about 0.7/10 missing γ-carboxylated glutamic acid sites, less than about 0.6/10 missing γ-carboxylated glutamic acid sites, less than about 0.5/10 missing γ-carboxylated glutamic acid sites, less than about 0.4/10 missing γ-carboxylated glutamic acid sites, less than about 0.3/10 missing γ-carboxylated glutamic acid sites, less than about 0.2/10 missing γ-carboxylated glutamic acid sites, less than about 0.1/10 missing γ-carboxylated glutamic acid sites, or no missing γ-carboxylated glutamic acid sites.

As described herein, the recombinant Factor II proteins suitably comprise less than about 20% thrombin, suitably less than about 15%, less than about 10%, less than about 5%, less than about 1%, less than about 0.5%, less than about 0.1%, less than about 0.05%, less than about 0.01%, less than about 0.005% or less than about 0.001% thrombin, based on total mass of the protein product. Suitably, the purified recombinant Factor II protein comprises less than about 10 thrombin, more suitably less than about 9 ng/ml thrombin, less than about 8 ng/ml thrombin, less than about 7 ng/ml thrombin, less than about 6 ng/ml thrombin, less than about 5 ng/ml thrombin, less than about 4 ng/ml thrombin, less than about 3 ng/ml thrombin, less than about 2 ng/ml thrombin, or less than about 1 ng/ml thrombin.

In embodiments, the purified recombinant prothrombin protein exhibits greater than about 50% bioactivity in a clotting assay (clot assay), as compared to a reference standard. Suitably, the purified recombinant prothrombin protein exhibits greater than about 60% bioactivity in a clotting assay, more suitably, greater than about 70% bioactivity in a clotting assay, greater than about 75% bioactivity in a clotting assay, greater than about 80% bioactivity in a clotting assay, greater than about 85% bioactivity in a clotting assay, greater than about 90% bioactivity in a clotting assay, or greater than about 95% bioactivity in a clotting assay.

In exemplary embodiments, the purified recombinant prothrombin protein exhibits greater than about 50% bioactivity in a calibrated automated thrombogram (CAT) assay, as compared to a reference standard. Suitably, the purified recombinant prothrombin protein exhibits greater than about 60% bioactivity in a CAT assay, more suitably, greater than about 70% bioactivity in a CAT assay, greater than about 75% bioactivity in a CAT assay, greater than about 80% bioactivity in a CAT assay, greater than about 85% bioactivity in a CAT assay, greater than about 90% bioactivity in a CAT assay, or greater than about 95% bioactivity in a CAT assay.

In further embodiments, the purified Factor II protein exhibits both greater than about 50% bioactivity in a clotting assay (clot assay) and greater than about 50% bioactivity in a calibrated automated thrombogram (CAT) assay.

Also provided are purified recombinant prothrombin proteins (Factor II) prepared by any process described herein. Suitably these Factor II proteins comprise less than about 0.5/10 missing γ-carboxylated glutamic acid sites, and are substantially free of thrombin.

It will be readily apparent to one of ordinary skill in the relevant arts that other suitable modifications and adaptations to the methods and applications described herein can be made without departing from the scope of any of the embodiments. The following examples are included herewith for purposes of illustration only and are not intended, to be limiting.

EXAMPLES

Example 1

Materials and Methods Related to Column Chromatography

The following are exemplary materials and methods related to the column chromatography methods described throughout.

Q SEPHAROSE™ Fast Flow Bind and Elute Chromatography (Q, B&E)

A Q SEPHAROSE™ Fast Flow column (GE Healthcare, Piscataway, N.J.) (QFF B&E) is equilibrated with 25 mM citrate, 30 mM sodium chloride, pH 6.0 prior to loading. Conditioned media is pH adjusted to pH 6.0 and loaded between 4-11 grams of product per L of resin at a linear velocity of 200 cm/h. The column is then re-equilibrated and washed with 25 mM citrate, 173 mM sodium chloride, pH 6.0. After washing, the column is eluted with a step to 25 mM citrate, 308 mM sodium chloride, pH 6.0.

Q SEPHAROSE™ Fast Flow Flowthrough Chromatography (Q, FT)

Q SEPHAROSE™ Fast Flow column is operated in flowthrough mode. The column is equilibrated in 25 mM citrate, 400 mM sodium chloride, pH 6.0 and then loaded with product at a linear velocity of 200 cm/h. The loading is typically between 2-6 grams of protein per L of resin. After loading the column is washed with equilibration buffer to collect the unbound product.

BAKERBOND™ XWP 500 PolyPEI-35 Bind and Elute Chromatography (PolyPEI)

A BAKERBOND™ XWP 500 Poly PEI-35 (poly(ethyleneimine)) column (column comprising poly(ethyleneimine) (PEI) bonded on a hydrophobic polymer (PolyPEI)) (AVANTOR™, Phillipsburg, N.J.) is pre-equilibrated with 125 mM HEPES, 4% (w/w) citrate, 0.5 M sodium chloride, pH 6.5 and then equilibrated with 25 mM HEPES, 4% (w/w) citrate, 0.5 M sodium chloride, pH 6.5. The column is then loaded with 5-12 grams of protein per L of resin at 140 cm/h. The column is washed with equilibration buffer and then with 25 mM HEPES, 4% (w/w) citrate, 1.04 M sodium chloride, pH 6.5. The product is then eluted in a linear gradient from 1M to 1.6-2.1 M sodium chloride.

Phenyl SEPHAROSE™ High Performance Bind and Elute Chromatography (Phenyl HP)

The column is equilibrated with 25 mM HEPES, 4% (w/w) citrate, 1 M sodium sulfate, pH 6.5. The eluate from the PEI column is adjusted to 1 M sodium sulfate and loaded between 1-12 grams of protein per L of resin at 100 cm/h. The column is re-equilibrated and then washed with 25 mM HEPES, 0.4% (w/w) citrate, 0.75 M sodium sulfate, pH 6.5. The column is then eluted in a gradient from 0.75 to 0 M sodium sulfate.

Hydroxyapatite Bind and Elute Chromatography (CHT)

The column is equilibrated with buffers containing low levels of sodium phosphate (10-50 and varying levels of sodium chloride (0.1-1 M NaCl) at pH 6.5. The column is loaded from 5-10 grams of protein per L of resin at 100 cm/h. After the loading, the column is equilibrated with the low phosphate buffer and varying concentrations of sodium chloride. The product is then eluted with an increasing linear gradient in phosphate concentration, up to 200-400 mM sodium phosphate at pH 6.5.

Example 2

Purification of Prothrombin

Recombinant human prothrombin (Factor II) (rhFII) protein is expressed in CHO cells and purified with a process that suitably includes four chromatography steps, a solvent/detergent viral inactivation step, a nanofiltration step, and an ultrafiltration/diafiltration step for final formulation. The schematic in FIG. 1 gives an overview of an exemplary purification process. The rhFII purification method shown in FIG. 1 has been scaled up from the bench scale to purify a 50 L bioreactor and a 500 L bioreactor.

Table 1 summarizes the relevant column and yield data from a representative 50 L purification. Due to the complex nature of the various samples being analyzed, three concentration methods were utilized to evaluate column performance. Total protein concentration by absorbance measured at 280 nm gives a measure of the total protein in a sample. It is the simplest method, and is used for samples after the Q SEPHAROSE™ Fast Flow flowthrough column (Q FT) since these samples are relatively pure (i.e. colorless samples with low levels of HCP). A second more time intensive method is a RP-HPLC method which can be used to measure the concentration of rhFII in any of the process intermediate samples. This concentration method was chosen mainly for crude samples (loads and pools from the first two columns) since it gives a measure of the mass of rhfII being loaded on to the early columns. The final concentration assay utilized for measuring performance of the rhFII purification process is the prothrombinase assay, which measures the concentration of active rhFII.

TABLE 1

Summary of column performance from a 50 L purification

| | Q B&E | Q FT | PolyPEI | Phenyl HP |
|---|---|---|---|---|
| Column Diameter (cm) | 10 | 10 | 7 | 7 |
| Column Volume (L) | 1.17 | 1.02 | 0.48 | 0.48 |
| Total Protein Loaded (g/L; by A280) | — | — | 10.6 | 5.9 |
| Product Loaded (g/L; by RP-HPLC) | 6.1 | 4.2 | — | — |
| Active Product Loaded (g/L) | 4.5 | 4.4 | 11.9 | 6.7 |
| Total Protein Yield (%) | — | — | 55.3 | 104.9 |
| Product Yield (%) | 59.9 | 130.7 | — | — |
| Active Product Yield (%) | 86.5 | 89.9 | 78.5 | 96.6 |

As can be seen in Table 1, the various concentration measurements result in very different step yield across the various columns, especially in the capture column where samples are much cruder compared to the later columns. As expected, the yield calculated over the capture column using RP-HPLC concentrations is much lower than yields calculated using the prothrombinase assay, suggesting that there is removal of impurities that are either not product related or less active than the desired product. On the other hand, the yield calculated over the Phenyl HP column using total protein concentration is very similar to the yield calculated from the prothrombinase assay concentration, suggesting that the load and pool from this column are very pure.

Table 2 summarizes relevant analytical impurity data from in-process product pools from the same 50 L purification. As seen in Table 2, the first two ion exchange columns remove a majority of the process related impurities, specifically host cell proteins (HCPs) and DNA and the Q SEPHAROSE™ FF flowthrough pool is mostly product and product related variants.

On the other hand, the levels of product related variants, particularly gamma-carboxylated variants as measured by HP-IEC pre-peak values, remain relatively unchanged over the first two columns. A typical level of IEC-HPLC pre-peak after the first two columns is around 40%, which is then loaded on to the PolyPEI column for enrichment of fully gamma-carboxylated product. This is accomplished through the use of a linear sodium chloride gradient to separate product with fewer gamma-carboxyalted sites (i.e., more missing gamma-carboxlated sites), which elute earlier in the gradient, from product with a higher level of gamma-carboxylation, which elute later in the gradient.

TABLE 2

Summary of impurities on process intermediates from a representative 50 L purification.

| | CM | Q B&E Pool | Q FT Pool | PolyPEI Pool | Phenyl HP Pool | DS |
|---|---|---|---|---|---|---|
| Total Protein (g/L)[1] | — | 1.66 | 1.34 | 0.78 | 1.74 | 11.00 |
| Product concentration (g/L)[2] | 0.12 | 1.28 | 1.50 | — | — | 11.18 |
| Active Product conc. (g/L)[3] | 0.087 | 1.339 | 1.079 | 0.894 | 1.831 | 9.563 |
| HCP (ng/mg) | — | 2266 | 2351 | <51 | <11 | 4 |
| DNA (ng/mg) | — | $2.1 \times 10^{-1}$ | $3.6 \times 10^{-1}$ | $1.5 \times 10^{-1}$ | $1.4 \times 10^{-2}$ | $2.4 \times 10^{-3}$ |
| Aggregates (%) | — | — | — | — | — | 0.3 |
| IEC prepeak (%) | — | 34.3 | 39.6 | 24.9 | 21.5 | 19.2 |
| Thrombin (ng/mg) | — | 2.4 | 5.0 | 2.7 | <0.5 | <0.2 |

TABLE 2-continued

Summary of impurities on process intermediates from a representative 50 L purification.

|  | CM | Q B&E Pool | Q FT Pool | PolyPEI Pool | Phenyl HP Pool | DS |
|---|---|---|---|---|---|---|
| Average missing gamma-carboxylation (out of 10 sites) | 0.6 | — | — | — | — | 0.38 |
| Fragment (%) | — | 3.0 | 2.6 | 2.8 | 1.4 | 1.4 |
| Sialic acid (mol NANA/mol) | — | 2.6 | 2.9 | 1.8 | 2.4 | 2.6 |
| CLOT Bioassay (%) | — | — | — | 83 | 106 | 110 |
| CAT Bioassay (%) | — | — | — | — | 69 | 108 |

[1]Concentration by absorbance at 280 nm.
[2]Concentration by RP-HPLC
[3]Concentration by prothrombinase assay The 50 L purification elution peak was fractionated with approximate 0.5-1.0 column volume fractions and mock pools were made and analyzed by HP-IEC. Table 3 gives HP-IEC pre-peak levels for individual fractions as well as mock pool made from individual fractions. As seen in Table 3, later eluting fractions and pools that contained later eluting fractions had lower levels of pre-peak on HP-IEC, which correlates to higher levels of gamma-carboxylation. An in-process control (IPC) strategy was used to fractionate the elution peak, analyze mock pools by HP-IEC, and carry forward the most inclusive pool that contained <25% pre-peak. This IPC control strategy allowed for the protein to meet the desired specification of <30% HP-IEC pre-peak since the remaining column (Phenyl HP) does not separate material with different levels of gamma-carboxylation. For this particular run, mock pool 3 (fractions 8-18) was carried forward. As a result of tightly controlled HP-IEC prepeak levels, the final drug substance material had low levels of missing gamma-carboxylation (an average of 0.38 out of 10 sites missing (0.38/10) gamma-carboxylation) and was highly active in both the CLOT and CAT bioassays.

TABLE 3

HP-IEC analysis of PolyPEI fractions and mock pools from 50 L purification run.

| Fraction or Mock pool | HP-IEC % pre-peak |
|---|---|
| Fraction 2 | 100% |
| Fraction 4 | 100% |
| Fraction 6 | 98.5% |
| Fraction 7 | 100% |
| Fraction 8 | 92.7% |
| Fraction 9 | 84.9% |
| Fraction 10 | 56.0% |
| Fraction 11 | 30.9% |
| Fraction 12 | 12.6% |
| Fraction 13 | 3.3% |
| Fraction 14 | 3.7% |
| Fraction 15 | 1.8% |
| Fraction 16 | 3.7% |
| Fraction 17 | 3.6% |
| Mock Pool 1 (Fractions 6-18) | 24.1% |
| Mock Pool 2 (Fractions 7-18) | 23.9% |
| Mock Pool 3 (Fractions 8-18) | 18.8% |
| Mock Pool 4 (Fractions 9-18) | 12.5% |
| Mock Pool 5 (Fractions 10-18) | 7.6% |
| Mock Pool 6 (Fractions 11-18) | 4.8% |
| Mock Pool 7 (Fractions 12-18) | 3.3% |
| Mock Pool 8 (Fractions 13-18) | 3.5% |

Example 3

Peptide Mapping of Recombinant Factor II

This example describes the peptide mapping analysis of recombinant human Factor II protein expressed in a CHO cell line.

Human recombinant Factor II contains several crucial post-translational modifications (PTMs) including γ-carboxylation of glutamic acid (Gla), glycosylation, and possible fragmentations. Due to their significant contribution to the function of Factor II, it is desirable to monitor these modifications during drug development.

For peptide mapping analysis, protein samples are treated with proteolytic enzymes to produce peptide fragments, which are separated and identified by HPLC-MS. By comparison with a Reference Standard, the application of peptide mapping assay to recombinant Factor II samples can confirm their primary structure and detect PTMs.

Materials and Methods

The method derives from a disulfide bond determination assay. Briefly, recombinant Factor II samples are incubated with N-Ethylmaleimide (NEM) to cap all possible free thiols, and then mixed with guanidine to denature the protein structure. The digestion procedure is performed by incubating proteins with endoproteinase Lysyl endopeptidase (Lys-C) overnight at neutral pH. The Lys-C fragments are separated by a reverse phase UPLC, and analyzed by a Thermo LTQ Orbitrap mass spectrometer.

Data and Discussion

As shown in Table 4, 25 Lys-C fragments are identified and cover about 75% of the Factor II sequence. The only significant gap encompasses residues 57-200 due to the lack of cleavage site in the region. It was determined that a 90-min HPLC gradient was efficient enough to separate all the fragments generated from reference standard and allow for MS measurement.

TABLE 4

Lys-C fragments from recombinant Factor II used in peptide mapping assay.

| Frag# | position | Retention time (min) | Observed Mass | Theoretical Mass | Peptide Sequence | SEQ ID NO: |
|---|---|---|---|---|---|---|
| K1 | 1-10 | 29.9 | 1294.64 | 1294.63 | ANTFLE*E*VRK(+2Gla) | 1 |
| K2 | 11-43 | 56.7 | 4095.58 | 4095.55 | GNLE*RE*CVE*E*TCSYE*E*AFE*ALE*SSTATDVFWAK(+8Gla) | 2 |
| K3 | 44-56 | 13.1 | 1511.74 | 1511.73 | YTACETARTPRDK | 3 |
| K6 | 201-204 | 8.4 | 418.27 | 418.27 | ALSK | 4 |
| K7K8 | 205-301 | 68.5 | 10826.74 | 10826.74 | HQDFNSAVQLVENFCRNPDGDEEGVWCYVAGKPGDFGYCDLYNYCEEAVEEETGDGLDEDSDRAIEGRTATSEYQTFFNPRTFGSGEADCGLRPLFEK | 5 |
| K10 | 303-307 | 9.3 | 591.30 | 591.30 | SLEDK | 6 |
| K11 | 308-341 | 57.6 | 3954.97 | 3954.97 | TERELLESYIDGRIVEGSDAEIGMSPWQVMLFRK | 7 |
| K12 | 342-372 | 77.9 | 3482.77 | 3482.76 | SPQELLCGASLISDRWVLTAAHCLLYPPWDK | 8 |
| K13 | 373-385 | 32.6 | 3578.56 | 3578.56 | N**FTENDLLVRIGK | 9 |
| K14 | 386-397 | 11.8 | 1588.84 | 1588.83 | HSRTRYERNIEK | 10 |
| K15 | 398-403 | 21.1 | 720.40 | 720.40 | ISMLEK | 11 |
| K16 | 404-424 | 38.6 | 2716.42 | 2716.41 | IYIHPRYNWRENLDRDIALMK | 12 |
| K17K18K19 | 425-455 | 44.7 | 3430.84 | 3430.85 | LKKPVAFSDYIHPVCLPDRETAASLLQAGYK | 13 |
| K18K19 | 427-455 | 45.8 | 3189.64 | 3189.66 | KPVAFSDYIHPVCLPDRETAASLLQAGYK | 14 |
| K19 | 428-455 | 49.0 | 3061.54 | 3061.55 | PVAFSDYIHPVCLPDRETAASLLQAGYK | 15 |
| K20 | 456-465 | 23.4 | 1087.60 | 1087.60 | GRVTGWGNLK | 16 |
| K21 | 466-474 | 20.2 | 1005.50 | 1005.50 | ETWTANVGK | 17 |

TABLE 4-continued

Lys-C fragments from recombinant Factor II used in peptide mapping assay.

| Frag# | position | Retention time (min) | Observed Mass | Theoretical Mass | Peptide Sequence | SEQ ID NO: |
|---|---|---|---|---|---|---|
| K22 | 475-494 | 49.1 | 2175.24 | 2175.23 | GQPSVLQV VNLPIVER- PVCK | 18 |
| K23K24 | 495-516 | 31.7 | 2517.19 | 2517.20 | DSTRIRITD NMFCAGYK PDEGK | 19 |
| K25 | 517-532 | 25.1 | 1625.72 | 1625.70 | RGDACEGD SGGPFVMK | 20 |
| K26 | 533-556 | 43.2 | 2802.28 | 2802.25 | SPFNNRWY QMGIVSWG EGCDRDGK | 21 |
| K27 | 557-567 | 33.7 | 1430.76 | 1430.76 | YGFYTHVF RLK | 22 |
| K28K29 | 568-572 | 14.7 | 702.44 | 702.45 | KWIQK | 23 |
| K29 | 569-572 | 14.6 | 574.33 | 574.33 | WIQK | 24 |
| K30 | 573-579 | 21.8 | 807.39 | 807.39 | VIDQFGE | 25 |

*Gla sites.
**N-glycosylation site N373.

Figures 5A, 5B:
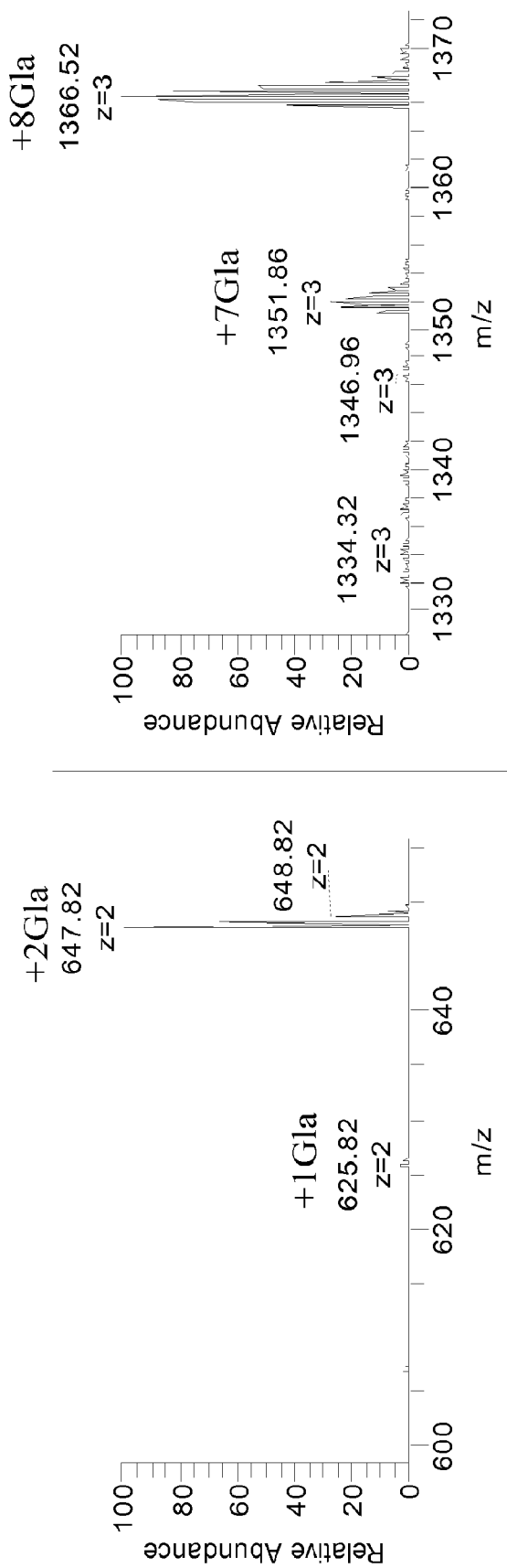
FIGS. 5A and 5B show γ-carboxylation of glutamic acid (Gla) at fragment K1 (5A) and K2 (5B) of recombinant Factor II.
Figure 6:
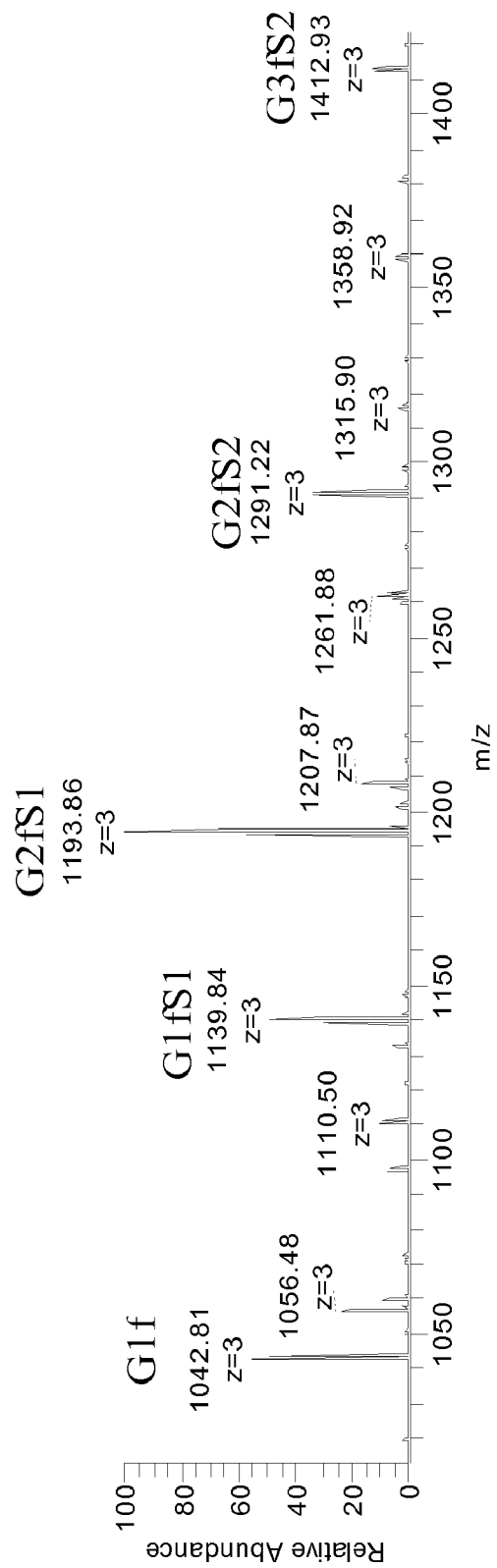
FIG. 6 shows the glycoprofile of fragment K13 (N373) of recombinant Factor II.

In addition to the confirmation of the primary structure, the assay can also be used to monitor important PTMs of recombinant Factor II. FIGS. 5A and 5B, show that the recombinant Factor II reference standard contains high Gla level at both fragment K1 and K2, while FIG. 6 displays the glycosylation profile of fragment K13. Based on these mass spectra, the approximate percentages of different species can be calculated using an extracted ion chromatogram.

These results provide a peptide mapping assay for recombinant Factor II, which can not only confirm the prime structure of the protein, but also monitor any modifications, such as Gla level and glycosylation profile.

Example 4

PolyPEI Chromatography and Thrombin Reduction on Hydrophobic Interaction Chromatography Poly(poly(ethyleneimine) (PolyPEI) (AVANTOR™, Phillipsburg N.J.) is a weak anion exchange resin that is run as bind and elute column in the recombinant Factor II purification process following solvent-detergent viral inactivation treatment. This chromatographic filtration is believed to remove residual solvent-detergent. It has been determined that the filtration also clears host cell proteins (HCPs) by two orders of magnitude, contributes to DNA clearance, removes thrombin, and if run in gradient mode, can enrich highly carboxylated (i.e., low levels of missing γ-carboxylated glutamic acid sites) and highly active recombinant Factor II.

The resin is equilibrated in 25 mM HEPES, 0.4% Sodium Citrate, 0.5 M Sodium Chloride, pH 6.5, and recombinant Factor II is loaded onto the anion exchange column to a load capacity of 5-12 g/L resin. This chromatography step is performed at a linear velocity of 140 cm/hr. The column is then rinsed with the same buffer, the washed with 25 mM HEPES, 0.4% Sodium Citrate, 1.04 M Sodium Chloride, pH 6.5, and finally eluted with a linear gradient to 25 mM HEPES, 0.4% citrate, 1.66 M NaCl, pH 6.5, over 12 column volumes.

The elution profile shows a broad peak with several front shoulders. During elution, individual fractions (with a size of approximately 0.5 column volume fractions) are collected and subjected to ion exchange (IEX) HPLC pre-peak analysis. Fractions eluting early in the gradient contain rhFII with a high IEC prepeak, indicating less complete carboxylation (and reduced bioactivity). These are excluded from the final product pool. Only those (later eluting) fractions containing recombinant Factor II with a low prepeak content are combined, such that the eluate pool contains recombinant Factor II with a prepeak content <25% (corresponding to less than 5% missing carboxylated glutamate residues (i.e., less than 0.5/10 missing) as determined by peptide mapping).

Charge Variant Separation

Recombinant Factor II contains 10 so-called "Gla-residues" in the N-terminal domain (see FIG. 2). These are γ-carboxylated glutamic acid (glutamate) residues are believed to be directly related to the biological activity of the protein. These residues are thought to chelate $Ca^{2+}$ ions, which mediates the protein's binding to phospholipid membranes, a prerequisite for recombinant Factor II activation to thrombin.

To investigate the relationship between posttranslational modification and bioactivity, a preparative separation of charge variants was performed by orthogonal methods. Individual fractions were subjected to bioactivity testing and analysis of posttranslational modifications by mass spectrometry and IEX HPLC. Recombinant Factor II was initially purified to 98.6% purity by a sequence of (1) Q capture anion exchange chromatography, (2) Q sepharose chromatography in flowthrough mode, (3) hydrophobic interaction chromatography on phenyl-sepharose in flowthrough mode and (4) poly(PEI) chromatography in bind-elute mode.

Several resins were evaluated for their potential to separate "charge variants", i.e. species of recombinant Factor II containing different degrees of carboxylation in the Gla-domain. The best techniques were found to be hydroxyapatite chromatography (CHT) (Table 5) and anion exchange chromatography on polyPEI (PPEI) (Table 6), both operated in linear gradient elution mode. For both chromatography processes, individual fractions were collected during elution and analyzed for (i) their prepeak content as determined by IEX HPLC, (ii) their extent of carboxylation/posttranslational modification by mass spectrometric peptide mapping, (iii) bioactivity in a Clot Assay, and (iv) bioactivity in a Calibrated Automated Thrombogram (CAT) assay.

The Clot Assay measures the time it takes to initiate clot formation upon addition of recombinant Factor II. In the method, the recombinant Factor II is added to Factor II-Deficient plasma (plasma containing all necessary coagulation factors except Factor II), in the presence of tissue factor, phospholipids, and $Ca^{2+}$ ions to stimulate clot formation. The ACL TOP Coagulation Analyzer measures clot formation by detecting the increase in optical density of the plasma sample which is caused by the initiation of clot formation. The time it takes to observe an increase in optical density to a set threshold in the assay, the prothrombin clot time (or PT Clot time), is recorded by the instrument and is directly proportional to the amount of Factor II that can form active thrombin present in the test sample. Each test sample is diluted by the instrument four times and the time to initiate clot formation of each dilution is determined by the instrument. The sample clot times are then plotted by the instrument and compared to a Reference Standard curve generated in the same way for each assay, log transformed, and similarity is assessed using parallel line analysis. If the sample and Reference Standard curves are parallel (have equivalent slopes), then the ratio of the intercepts of the Reference Standard Curve and Test Sample Curve determine the potency of the Factor II test sample. Recombinant Factor II test sample potency is also reported as a specific activity (IU/mg) by comparison to the WHO Prothrombin International Standard (from NIBSC).

The Calibrated Automated Thrombogram (CAT) assay is a thrombin generation assay used to determine the thrombin generation potential of recombinant Factor II. Samples are diluted to four concentrations and each sample dilution is measured in triplicate. Factor II deficient platelet poor plasma and a 'trigger solution' (containing Tissue Factor, $Ca^{2+}$, phospholipid vesicles) are added to the samples. Calibrator wells are set up using Factor II-deficient plasma, assay buffer, and an amidolytic agent (thrombin calibrator) for data correction. Next, a slow fluorogenic thrombin substrate is added to all wells. As prothrombin is converted to thrombin, thrombin cleaves the fluorescent substrate. Cleaved substrate fluoresces and this fluorescence is detected by the Fluoroskan Ascent Fluorometer equipped with Thrombinoscope Software. Fluorescence of each assay well is measured every 20 seconds for 60 minutes. The Endogenous Thrombin Potential (ETP) of the recombinant Factor II is measured for each sample at the four concentrations. The relative potency of the samples is determined by the slope-ratio method. The slope for each sample is calculated by plotting the value of the ETP versus each of the four concentrations. A best fit line is generated, giving the slope of each sample. The slope of the samples is compared to the slope of the reference standard and results are reported as percent relative potency. The percent relative potency is used to determine the specific activity of the recombinant Factor II samples relative to the plasma derived WHO Factor II international standard.

TABLE 5

Results following CHT chromatography.

| Sample description | IEC pre-peak | Peptide Mapping Total Missing Gla | Bioactivity | |
|---|---|---|---|---|
| | | | Clot Assay | CAT Assay |
| Initial purified FII (starting material for charge variant separation) | 36.25 | 0.7 | 70% | 57% |
| A CHT Fr. C9C12 | 90.7% | 1.35 | 23% | 24% |
| B CHT Fr. D9D6 | 22.3% | 0.5 | 78% | 57% |
| C CHT Fr. D5D2 | 10.6% | 0.29 | 106% | 78% |
| D CHT Fr. D1E4 | 14.7% | 0.37 | 98% | 53% |

TABLE 6

Results following PolyPEI chromatography.

| Sample description | IEC pre-peak | Peptide Mapping Total Missing Gla | Bioactivity | |
|---|---|---|---|---|
| | | | Clot Assay | CAT Assay |
| Initial purified FII (starting material for charge variant separation) | 36.25 | 0.7 | 70% | 57% |
| A PPEI Fraction C5C7 | 24.5% | 1.31 | 21% | 25% |
| B PPEI Fraction C8C9 | 29.8% | 0.51 | 81% | 63% |
| C PPEI Fraction C10C11 | 1.8% | 0.18 | 106% | 81% |
| D PPEI Fraction C12D12 | 3.7% | 0.14 | 119% | 87% |

Figure 3:
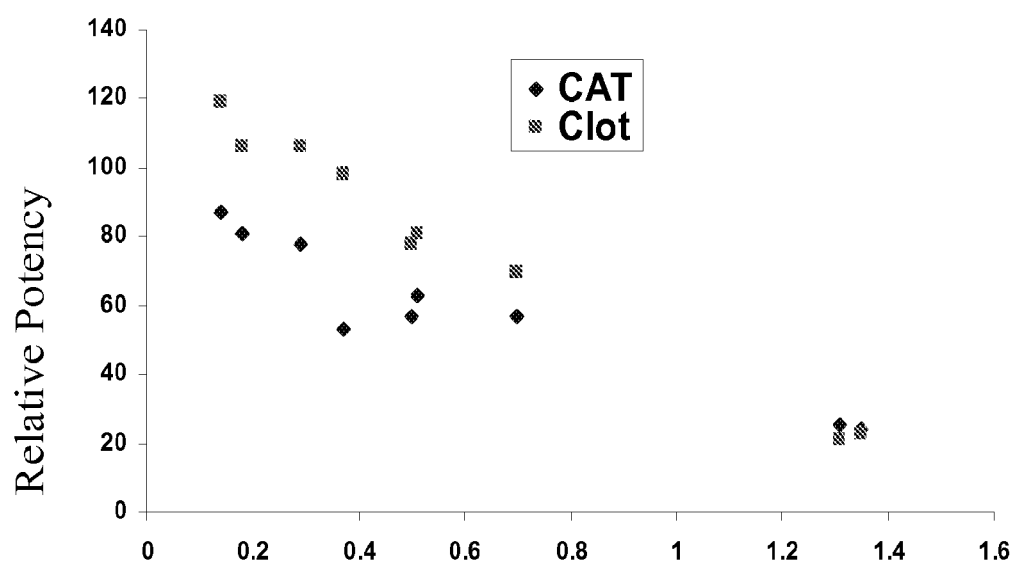
FIG. 3 shows the extent of posttranslational carboxylation relative to the relative potency (in vitro bioactivity) in the Clot and CAT bioassay of recombinant prothrombin.

A strong correlation is observed between the extent of posttranslational carboxylation and the relative potency (in vitro bioactivity) in the Clot and CAT bioassay, as demonstrated in FIG. 3, showing the relationship between relative potency and missing Gla (X/10). This indicates the benefits of process control in combined upstream and downstream processing for recombinant Factor II in order to generate a highly carboxylated product.

When the in vitro bioactivity of recombinant Factor II in the course of purification is monitored by the CAT bioassay, a significant "activation" is observed following the PolyPEI chromatography step, as shown in Table 7.

TABLE 7

Activity in CAT and Clot Assay Following Filtration

| Purification Sequence | Activity in CAT Assay | Activity in Clot Assay |
|---|---|---|
| Q B&E | 5% | 100-115% |
| Q FT | 5% | 100-115% |
| Phenyl HP | 15% | 100-115% |
| PolyPEI | 95-120% | 110-130% |

Figure 4:
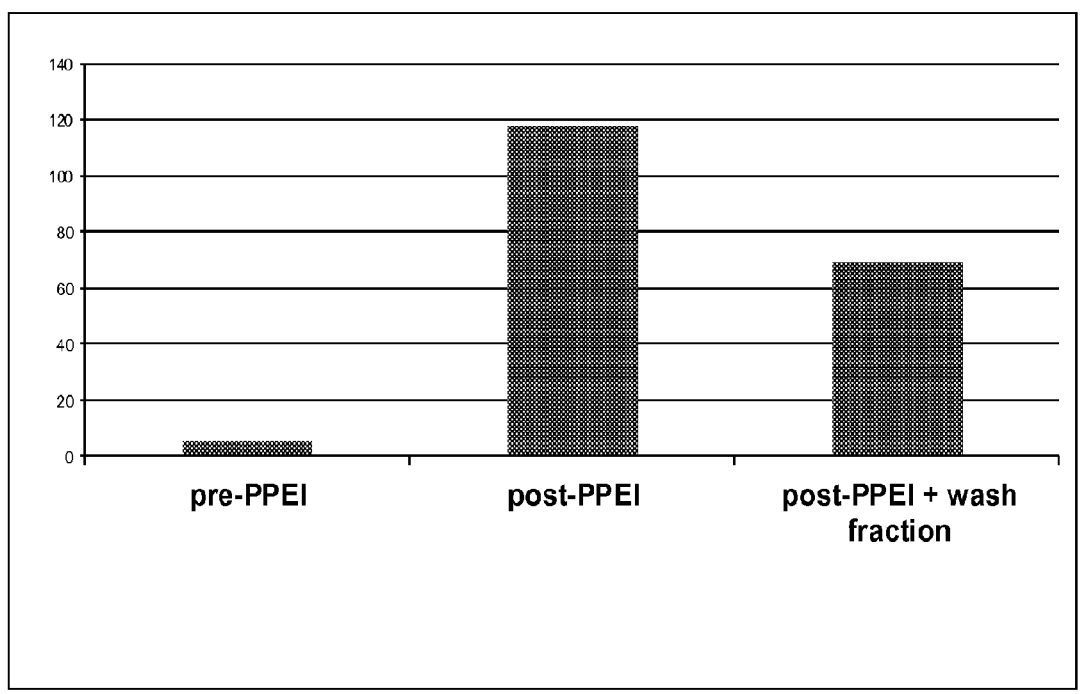
FIG. 4 shows the results of the CAT bioassay as a function of filtering with a poly(PEI) column.

When the "wash fraction" removed during PolyPEI chromatography is re-added to the purified eluate from this column, a reduction in bioactivity can be observed, as shown in FIG. 4, pointing to the possibility that this column removes an inhibitory contaminant.

Similar "activation" of recombinant Factor II can be achieved on other chromatography resins when operated in bind-elute inode, including blue sepharose, phenyl sepharose and capto adhere.

Finally, hydrophobic interaction chromatography was performed on phenyl sepharose HP resin (GE Healthcare), operated in bind-elute mode. This column serves to remove fragment 1, thrombin, residual contaminant host cell proteins and DNA. Sodium sulfate is used as lyotropic salt, and load preparation is performed by adding 2 parts load adjustment buffer (25 mM HEPES, 0.4% citrate, 1 M Sodium sulfate, 1.86 M Sodium chloride, pH 6.5) to 3 parts Poly-PEI eluate. The phenyl sepharose column is equilibrated in 25 mM HEPES, 0.4% Sodium Citrate, 1.0 M Sodium Sulfate, pH 6.5, and adjusted rhFII is loaded onto the column to a capacity of 3-10 g/L resin. The column is subsequently rinsed with the same buffer, then washed with 25 mM HEPES, 0.4% Sodium Citrate, 0.75 M Sodium Sulfate, pH 6.5. Elution is performed with a linear gradient to 25 mM HEPES, 0.4% Sodium Citrate, pH 6.5, over 6 CVs. Recombinant Factor II eluted from the hydrophobic interaction column is recovered, concentrated and formulated, by diafiltration or other suitable method known to one skilled in the art, to provide a final purified recombinant Factor II product.

Thrombin spike studies indicate that anion exchange chromatography on polyPEI is useful for reducing the thrombin content in the preparation. Commercially available thrombin (Enzyme Research Laboratories, HT 3564A; 3059 units/mg) was added to the load of the PolyPEI column, and the thrombin content in column flowthrough (non-binding fraction), wash and ciliate fraction was measured. Both a chromogenic and a fluorescent assay for thrombin activity were employed.

The starting material was recombinant Factor II, recovered from the Q Flowthrough column and treated with solvent-detergent. 56.67 g of this material (at a concentration of 2.8 mg/ml) was spiked with 1 ug of thrombin and loaded directly onto the PolyPEI column, equilibrated in 25 mM HEPES, 0.5 M NaCl, 0.4% citrate, pH 6.5. The column was washed with 25 mM HEPES, 1.04 M NaCl, 0.4% citrate, pH 6.5, and subsequently eluted with a linear gradient to 1.86 M NaCl (in the same buffer) over 12 column volumes. The eluate peak was collected.

In the column load, thrombin content was determined as 70 ng/ml (using the chromogenic assay). In the eluate fraction, thrombin content was found to be below the limit of quantitation for the more sensitive fluorescent assay (<1.876 ng/ml). No thrombin was detected in the column wash fraction. Thrombin could only be detected in the flowthrough from this column (non-bound fraction), were it was measured as 3.6 ng/ml. This result (and data from repeated experiments) suggests that under the buffer conditions employed in the process, thrombin does not bind to the polyPEI column and is separated from recombinant Factor II that binds very tightly.

Example 5

Control of IEC Prepeak Content Using PolyPEI in Linear Gradient Elution Mode

The ion exchange chromatography (IEC) prepeak observed for recombinant Factor II is indicative of the extent of carboxylation of the ten glutamate residues in the so-called "Gla-domain." A high IEC-prepeak points to a large percentage of molecules missing carboxylated glutamate residues and correlates with a lower bioactivity.

A linear gradient elution on the weak anion exchange resin PolyPEI allows for selectively enriched, highly carboxylated and highly active recombinant Factor II, which elutes later in the gradient compared to undercarboxylated protein. During elution, fractions are collected and analyzed by IEX HPLC. Early eluting fractions showing a high IEC prepeak are not combined in the eluate pool.

Column load was the protein preparation after Q B&E and Q FT chromatography, followed by solvent-detergent treatment. IEC prepeak in this material was determined as 39.6%. The PolyPEI resin was equilibrated in 25 mM HEPES, 0.5 M NaCl, 0.4% citrate, pH 6.5. 4.1 g of recombinant Factor II at a concentration of 1.2 g/L was loaded onto the column (with a CV of 0.48 L) at a flow rate of 140 cm/hr. The column was rinsed with the same buffer, then washed with 25 mM HEPES, 1.04 M NaCl, 0.4% citrate, pH 6.5, and subsequently eluted with a gradient to 1.86 M NaCl over 12 column volumes. During gradient elution, fractions with an individual volume of 0.5 CV (approximately 250 ml) were collected and analyzed by IEX HPLC.

Table 8 shows prepeak values determined by IEX HPLC for individual eluate fractions.

TABLE 8

| IEC Prepeak Values | |
|---|---|
| Eluate Fraction | IEC Pre-peak |
| 2 | 100% |
| 6 | 98.5% |
| 8 | 92.7% |
| 10 | 56% |
| 12 | 12.6% |
| 14 | 3.7% |

Fractions 8-18 were combined to generate an eluate pool with an IEC prepeak of 24.9%. Step yield as determined by A280 UV absorbance, was 55.3%, as determined by PTase assay 78.5%.

Example 6

Scale Up of Prothrombin Purification Process

The rhFII purification process described in Example 1 was scaled up to purify a 500 L bioreactor. Table 9 summarizes the column performance data from the 500 L purification. To keep loading similar to the 50 L purification, the columns were scaled by a factor of roughly 10.

TABLE 9

| Summary of column performance from a 500 L purification. | | | | |
|---|---|---|---|---|
|  | QFF B&E | QFF FFT | PolyPEI | Phenyl HP |
| Column Diameter (cm) | 30 | 30 | 25 | 25 |
| Column Volume (L) | 9.2 | 9.2 | 6.7 | 6.4 |
| Total Protein Loaded (g/L; by A280) | — | — | 5.3 | 3.4 |
| Product Loaded (g/L; by RP-HPLC) | 6.4 | 3.5 | — | — |
| Active Product Loaded (g/L) | 3.1 | 2.6 | 4.8 | 2.7 |
| Total Protein Yield (%) | — | — | 72.7 | 111.5 |
| Product Yield (%) | 54.8 | 88.6 | — | — |
| Active Product Yield (%) | 84.8 | 101.4 | 97.2 | 130.7 |

Table 10 shows the impurity levels in process intermediates. Similar to the 50 L purification described previously, the level of gamma-carboxylation after the Q Sepharose FF flow through column was around 33.5% HP-IEC prepeak and loaded on to the PolyPEI column for enrichment of gamma-carboxylation. A comparison of the chromatographic behavior at the 500 L scale purification with the 50

L scale purification and the bench scale purification under similar operating conditions shows a very robust separation on PolyPEI. At all scales multiple early eluting species can be observed; however the relative amounts of each early eluting species is dependent on the material being loaded on to the PolyPEI column. Table 10 summarizes the HP-IEC prepeak levels for individual fractions and mock pools from the 500 L scale purification. As with the smaller scale runs (50 L and bench scale runs), the early eluting fractions and mock pools containing earlier fractions had higher levels of prepeak, which corresponds to higher levels of missing gamma-carboxylation. For this run, Mock Pool #2 (fractions 2-15) was carried forward to Phenyl chromatography.

TABLE 10

Summary of impurities on process intermediates from a representative 500 L batch.

|  | CM | QFF B&E Pool | QFF FFT Pool | PPEI Pool | Phenyl Pool | DS |
|---|---|---|---|---|---|---|
| Total Protein (g/L)[1] | — | 1.01 | 1.10 | 0.50 | 1.42 | 9.86 |
| Product concentration (g/L)[2] | 0.11 | 1.17 | 0.99 | — | — | — |
| Active Product conc. (g/L)[3] | 0.053 | 0.872 | 0.645 | 0.392 | 1.305 | 9.036 |
| HCP (ng/mg) | — | 3517 | 3173 | <80 | <28 | <8 |
| DNA (ng/mg) | — | $3.0 \times 10^{-1}$ | $2.7 \times 10^{-1}$ | $2.3 \times 10^{-1}$ | $5.6 \times \times 10^{-4}$ | $2.7 \times 10^{-4}$ |
| Aggregates (%) | — | 1.2 | 1.5 | 0.9 | 0.1 | 0.2 |
| IEC prepeak (%) | — | 32.6 | 33.5 | 22.9 | 20.9 | 17.0 |
| Thrombin (ng/mg) | — | 5.6 | 3.7 | <0.5 | <0.2 | 0.1 |
| Missing GLA | 0.61 | — | — | — | — | 0.50 |
| Fragment (%) | — | — | 1.1 | 0.9 | 0.5 | 0.4 |
| Sialic acid (mol NANA/mol) | — | 3.4 | 1.8 | 1.6 | 1.6 | 2.0 |
| CLOT Bioassay (%) | — | — | — | — | 84 | 94 |
| CAT Bioassay (%) | — | — | — | — | 55 | 83 |

[1]Concentration by absorbance at 280 nm.
[2]Concentration by RP-HPLC.
[3]Concentration by prothrombinase assay.

Table 12 summarizes the product quality of representative 50 L and 500 L batches. The final drug substance meets release specifications for all process related impurities (HCP, DNA) and all product related impurities (aggregates, fragments, gamma-carboxylated variants, and sialated variants) which resulted in product that was highly active in the clotting bioassay.

TABLE 12

Summary of drug substance material generated from representative 50 L and 500 L batches.

|  | 50 L #1 | 50 L #2 | 500 L #3 | 500 L #4 |
|---|---|---|---|---|
| Total protein (g/L)[1] | 11.0 | 9.82 | 9.74 | 9.86 |
| Active Product conc. (g/L)[2] | 9.56 | 9.55 | 10.36 | 9.04 |
| HCP (ng/mg) | 4 | 4 | 8 | <8 |
| DNA (ng/mg) | $2.4 \times 10^{-3}$ | $3.7 \times 10^{-2}$ | $9.7 \times 10^{-4}$ | $2.7 \times 10^{-4}$ |
| Aggregates (%) | 0.3 | 0.2 | 0.1 | 0.2 |
| IEC prepeak (%) | 19.2 | 23.9 | 22.0 | 17.0 |
| Thrombin (ng/mg) | <0.2 | 0.1 | 0.3 | 0.1 |
| Missing GLA | 0.38 | 0.46 | 0.33 | 0.50 |
| Fragment (%) | 1.4 | 0.4 | 0.4 | 0.4 |
| Sialic acid (mol NANA/mol) | 2.6 | 3.3 | 2.5 | 2.0 |
| CLOT Bioassay (%) | 110 | 105 | 118 | 94 |
| CAT Bioassay (%) | 108 | 121 | 121 | 83 |

[1]Concentration by absorbance at 280 nm.
[2]Concentration by prothrombinase assay Example 7

Enrichment of Gamma-Carboxylated Variants with Hydroxyapatite Chromatography

As an alternative to PolyPEI chromatography, hydroxyapatite was investigated for its ability to enrich gamma-carboxylated species. Recombinant Factor II binds strongly to hydroxyapatite and is not eluted with increased sodium chloride, even in concentrations up to 1M. However, an increase in phosphate ion concentration can successfully elute recombinant Factor II from the hydroxyapatite column. Table 11 summarizes bench scale hydroxyapatite runs.

The load material for all runs was the same and included 37.9% HP-IEC prepeak, which corresponds to material with lower average level of gamma-carboxylation. In all three hydroxyapatite chromatography runs eluted with phosphate gradients, a front shoulder is observed, much like the behavior of recombinant Factor II in sodium chloride gradients on PolyPEI chromatography. The runs were each fractionated and mock pools were made. Pool 1 contained a majority of the early eluting fractions while Pool 2 contained a majority of the main peak. Mock pools of the complete elution peak were also made (Pools 1 and 2 combined). Samples of the pools were tested by HP-IEC to determine the level of HP-IEC prepeak.

As seen in Table 11, pools containing early eluting fractions (early/pool #1 and complete pools 1 and 2) had higher levels of HP-IEC pre peak than the main pool (#2). This is similar to the enrichment of gamma-carboxylation which occurs in anion exchange chromatography on PolyPEI. Unlike anion exchange chromatography where the separation of charged variants occurs in a sodium chloride gradient, the effect of sodium chloride on separation in hydroxyapatite is much less noticeable. For example, rhFII elutes earlier in the phosphate gradient in the presence 1 M sodium chloride compared to 0.1 M sodium chloride; however, there is negligible impact on the separation of gamma-carboxylated variants based on the similar peak shapes and HP-IEC prepeak levels in the main pools. This suggests that the mechanism or the interaction between rhfII and hydroxyapatite is multi-modal and includes some ionic interactions.

TABLE 11

Summary of enrichment of gamma-carboxylated recombinant Factor II on hydroxyapatite

| Run # | [NaCl] (M) | [Phosphate] Gradient (mM) | Loading (g/L) | Gradient CV | Bed height (cm) | Pools Early (1) | Pools Main (2) | Pools Complete (1 + 2) |
|---|---|---|---|---|---|---|---|---|
| 1 | 0.1 | 50-400 | 10 | 10 | 10 | — | 15.3 | 28.6 |
| 2 | 1.0 | 50-400 | 10 | 10 | 10 | — | 17.6 | 27.6 |
| 3 | 1.0 | 50-250 | 5 | 10 | 20 | 93.8 | 24.0 | 37.9 |

The effect of column loading, residence time, and phosphate gradient slope were also investigated. For this determination, the loading was decreased from 10 grams of recombinant Factor II per L of resin to 5 grams of recombinant Factor II per L of resin, the residence time was doubled (from 6 minutes to 12 minutes), and the phosphate slope was decreased by 150 mM phosphate over 10 column volumes. Under these conditions, the early eluting shoulder, which contains lower levels of gamma-carboxylation, was more resolved. Moreover, the early eluting material likely contained varying levels of missing gamma-carboxylation based on the fact that multiple shoulders were observed. It is unclear which of these operational condition changes was responsible for the increased resolution, but most likely each change added to the improved resolution.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

What is claimed is:

1. A method for purifying a recombinant coagulation factor protein, the method comprising: a) providing a mixture comprising the recombinant coagulation factor protein; b) filtering the mixture through at least a first anion exchange column to produce a first anion exchange column product; c) loading the first anion exchange column product onto a poly(ethyleneimine) (PEI) column and eluting with a linear sodium chloride gradient to produce one or more fractions of a PEI column product; and d) recovering one or more fractions of PEI column product with a combined pre-peak of less than 30% to obtain the purified recombinant coagulation factor protein, wherein the purified recombinant coagulation factor protein comprises less than about 0.8/10, 0.7/10, 0.6/10, 0.5/10 or 0.4/10 missing D-carboxylated glutamic acid sites and wherein the pre-peak of one or more PEI column product is determined by high performance liquid chromatography (HPLC).

2. The method of claim 1, wherein the recombinant coagulation factor protein is prothrombin (Factor II).

3. The method of claim 1, wherein the mixture is a filtered mixture from a bioreactor.

4. The method of claim 1, wherein the filtering through the first anion exchange column comprises a binding and elution filtering.

5. The method of claim 1, wherein the filtering further comprises filtering the first anion exchange column product through a second anion exchange column to produce a second anion exchange column product.

6. The method of claim 5, wherein the filtering through the second anion exchange column comprises a flow-through filtering.

7. The method of claim 1, further comprising inactivating the first anion exchange column product and/or the PEI column product with a solvent/detergent inactivation before c).

8. The method of claim 1, further comprising filtering the PEI column product through a hydrophobic interaction column (HIC).

9. The method of claim 8, wherein the filtering of the PEI column product comprises a binding and elution filtering.

10. The method of claim 1, further comprising nanofiltering.

11. The method of claim 2, wherein the recombinant prothrombin protein is substantially free of thrombin.

12. The method of claim 1, wherein the purified recombinant coagulation factor protein comprises less than about 0.4/10 missing D-carboxylated glutamic acid sites.

13. A method for purifying a recombinant coagulation factor protein, the method comprising: a) providing a mixture comprising the recombinant coagulation factor protein; b) filtering the mixture through at least a first anion exchange column to produce a first anion exchange column product; c) inactivating the first anion exchange column product with a solvent/detergent viral inactivation to produce an inactivated mixture; d) loading the inactivated mixture onto a poly (ethyleneimine) (PEI) column and eluting with a linear sodium chloride gradient to produce one or more fractions of a PEI column product; e) recovering one or more fractions of PEI column product with a combined pre-peak of less than 30% to form a low pre-peak content PEI column product, wherein the pre-peak of one or more PEI column product is determined by high performance liquid chromatography (HPLC); f) filtering the low pre-peak content PEI column product through a hydrophobic interaction column (HIC) to produce a hydrophobic interaction column (HIC) product; g) filtering the HIC product; and h) recovering the purified recombinant coagulation factor protein, wherein the purified recombinant coagulation factor protein comprises less than about 0.8/10, 0.7/10, 0.6/10, 0.5/10 or 0.4/10 missing D-carboxylated glutamic acid sites.

14. The method of claim 13, wherein the recombinant coagulation factor protein is prothrombin (Factor II).

15. The method of claim 13, wherein the mixture is a filtered mixture from a bioreactor.

16. The method of claim 13, wherein the filtering through at least a first anion exchange column in b) comprises a binding and elution filtering.

17. The method of claim 13, wherein the filtering in b) further comprises filtering the first anion exchange column product through a second anion exchange column.

18. The method of claim 17, wherein the filtering through a second anion exchange column comprises a flow-through filtering.

19. The method of claim 13, wherein the filtering in f) comprises a binding and elution filtering.

20. The method of claim 13, wherein the filtering in g) comprises nano filtering.

21. The method of claim 14, wherein the recombinant prothrombin protein is substantially free of thrombin.

22. The method of claim 13, wherein the purified recombinant coagulation factor protein comprises less than about 0.4/10 missing D-carboxylated glutamic acid sites.

23. A method for purifying a recombinant prothrombin (Factor II) protein, the method comprising: a) providing a filtered mixture from a bioreactor comprising the recombinant prothrombin protein; b) binding and elution filtering the mixture through a first anion exchange column to produce a first anion exchange column product; c) flowthrough filtering the first anion exchange column product through a second anion exchange column to produce a second anion exchange column product; d) inactivating the second anion exchange column product with a solvent/detergent viral inactivation to produce an inactivated mixture; e) loading the inactivated mixture onto a poly(ethyleneimine) (PEI) column and eluting with a linear sodium chloride gradient to produce one or more fractions of a PEI column product; f) recovering one or more fractions of PEI column product with a combined pre-peak of less than 30% to form a low pre-peak content PEI column product, wherein the pre-peak of one or more PEI column product is determined by high performance liquid chromatography (HPLC); g) binding and elution filtering the low pre-peak content PEI column product through a hydrophobic interaction column (HIC) to produce a HIC product; h) nanofiltering the HIC product; and i) recovering the purified recombinant prothrombin protein, wherein the purified recombinant prothrombin protein (Factor II) comprises less than about 0.8/10, 0.7/10, 0.6/10, 0.5/10 or 0.4/10 missing D-carboxylated glutamic acid sites.

24. The method of claim 23, wherein the recombinant prothrombin protein is substantially free of thrombin.

25. The method of claim 23, wherein the purified recombinant prothrombin protein comprises less than about 0.7/10, 0.6/10, 0.5/10 or 0.4/10 missing D-carboxylated glutamic acid sites.

26. A purified recombinant prothrombin protein (Factor II) comprising less than about 0.5/10 missing D-carboxylated glutamic acid sites and that is substantially free of thrombin, prepared by the method according to claim 1.

27. A purified recombinant prothrombin protein (Factor II) comprising less than about 0.5/10 missing D-carboxylated glutamic acid sites and that is substantially free of thrombin, prepared by the method of claim 13.

28. A purified recombinant prothrombin protein (Factor II) comprising less than about 0.5/10 missing D-carboxylated glutamic acid sites and that is substantially free of thrombin, prepared by the method of claim 23.

* * * * *

SEQUENCE LISTING

```
<160> NUMBER OF SEQ ID NOS: 25

<210> SEQ ID NO 1
<211> LENGTH: 10
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: gamma-carboxyglutamic acid

<400> SEQUENCE: 1

Ala Asn Thr Phe Leu Glu Glu Val Arg Lys
1               5                   10

<210> SEQ ID NO 2
<211> LENGTH: 33
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: gamma-carboxyglutamic acid
<220> FEATURE:
<221> NAME/KEY: MOD_RES
<222> LOCATION: (6)..(6)
<223> OTHER INFORMATION: gamma-carboxyglutamic acid
<220> FEATURE:
<221> NAME/KEY: MOD_RES
<222> LOCATION: (9)..(10)
<223> OTHER INFORMATION: gamma-carboxyglutamic acid
<220> FEATURE:
<221> NAME/KEY: MOD_RES
<222> LOCATION: (15)..(16)
<223> OTHER INFORMATION: gamma-carboxyglutamic acid
<220> FEATURE:
<221> NAME/KEY: MOD_RES
<222> LOCATION: (19)..(19)
<223> OTHER INFORMATION: gamma-carboxyglutamic acid
<220> FEATURE:
<221> NAME/KEY: MOD_RES
<222> LOCATION: (22)..(22)
<223> OTHER INFORMATION: gamma-carboxyglutamic acid
```

<400> SEQUENCE: 2

Gly Asn Leu Glu Arg Glu Cys Val Glu Thr Cys Ser Tyr Glu Glu
1               5                   10                  15

Ala Phe Glu Ala Leu Glu Ser Ser Thr Ala Thr Asp Val Phe Trp Ala
            20                  25                  30

Lys

<210> SEQ ID NO 3
<211> LENGTH: 13
<212> TYPE: PRT
<213> ORGANISM: Homo sapiens

<400> SEQUENCE: 3

Tyr Thr Ala Cys Glu Thr Ala Arg Thr Pro Arg Asp Lys
1               5                   10

<210> SEQ ID NO 4
<211> LENGTH: 4
<212> TYPE: PRT
<213> ORGANISM: Homo sapiens

<400> SEQUENCE: 4

Ala Leu Ser Lys
1

<210> SEQ ID NO 5
<211> LENGTH: 97
<212> TYPE: PRT
<213> ORGANISM: Homo sapiens

<400> SEQUENCE: 5

His Gln Asp Phe Asn Ser Ala Val Gln Leu Val Glu Asn Phe Cys Arg
1               5                   10                  15

Asn Pro Asp Gly Asp Glu Glu Gly Val Trp Cys Tyr Val Ala Gly Lys
            20                  25                  30

Pro Gly Asp Phe Gly Tyr Cys Asp Leu Asn Tyr Cys Glu Glu Ala Val
        35                  40                  45

Glu Glu Glu Thr Gly Asp Gly Leu Asp Glu Asp Ser Asp Arg Ala Ile
    50                  55                  60

Glu Gly Arg Thr Ala Thr Ser Glu Tyr Gln Thr Phe Phe Asn Pro Arg
65                  70                  75                  80

Thr Phe Gly Ser Gly Glu Ala Asp Cys Gly Leu Arg Pro Leu Phe Glu
                85                  90                  95

Lys

<210> SEQ ID NO 6
<211> LENGTH: 5
<212> TYPE: PRT
<213> ORGANISM: Homo sapiens

<400> SEQUENCE: 6

Ser Leu Glu Asp Lys
1               5

<210> SEQ ID NO 7
<211> LENGTH: 34
<212> TYPE: PRT
<213> ORGANISM: Homo sapiens

<400> SEQUENCE: 7

```
Thr Glu Arg Glu Leu Leu Glu Ser Tyr Ile Asp Gly Arg Ile Val Glu
1               5                   10                  15

Gly Ser Asp Ala Glu Ile Gly Met Ser Pro Trp Gln Val Met Leu Phe
                20                  25                  30

Arg Lys

<210> SEQ ID NO 8
<211> LENGTH: 31
<212> TYPE: PRT
<213> ORGANISM: Homo sapiens

<400> SEQUENCE: 8

Ser Pro Gln Glu Leu Leu Cys Gly Ala Ser Leu Ile Ser Asp Arg Trp
1               5                   10                  15

Val Leu Thr Ala Ala His Cys Leu Leu Tyr Pro Pro Trp Asp Lys
                20                  25                  30

<210> SEQ ID NO 9
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: N-glycosylation site N373

<400> SEQUENCE: 9

Asn Phe Thr Glu Asn Asp Leu Leu Val Arg Ile Gly Lys
1               5                   10

<210> SEQ ID NO 10
<211> LENGTH: 12
<212> TYPE: PRT
<213> ORGANISM: Homo sapiens

<400> SEQUENCE: 10

His Ser Arg Thr Arg Tyr Glu Arg Asn Ile Glu Lys
1               5                   10

<210> SEQ ID NO 11
<211> LENGTH: 6
<212> TYPE: PRT
<213> ORGANISM: Homo sapiens

<400> SEQUENCE: 11

Ile Ser Met Leu Glu Lys
1               5

<210> SEQ ID NO 12
<211> LENGTH: 21
<212> TYPE: PRT
<213> ORGANISM: Homo sapiens

<400> SEQUENCE: 12

Ile Tyr Ile His Pro Arg Tyr Asn Trp Arg Glu Asn Leu Asp Arg Asp
1               5                   10                  15

Ile Ala Leu Met Lys
                20

<210> SEQ ID NO 13
<211> LENGTH: 31
<212> TYPE: PRT
<213> ORGANISM: Homo sapiens
```

```
<400> SEQUENCE: 13

Leu Lys Lys Pro Val Ala Phe Ser Asp Tyr Ile His Pro Val Cys Leu
1               5                   10                  15

Pro Asp Arg Glu Thr Ala Ala Ser Leu Leu Gln Ala Gly Tyr Lys
            20                  25                  30

<210> SEQ ID NO 14
<211> LENGTH: 29
<212> TYPE: PRT
<213> ORGANISM: Homo sapiens

<400> SEQUENCE: 14

Lys Pro Val Ala Phe Ser Asp Tyr Ile His Pro Val Cys Leu Pro Asp
1               5                   10                  15

Arg Glu Thr Ala Ala Ser Leu Leu Gln Ala Gly Tyr Lys
            20                  25

<210> SEQ ID NO 15
<211> LENGTH: 28
<212> TYPE: PRT
<213> ORGANISM: Homo sapiens

<400> SEQUENCE: 15

Pro Val Ala Phe Ser Asp Tyr Ile His Pro Val Cys Leu Pro Asp Arg
1               5                   10                  15

Glu Thr Ala Ala Ser Leu Leu Gln Ala Gly Tyr Lys
            20                  25

<210> SEQ ID NO 16
<211> LENGTH: 10
<212> TYPE: PRT
<213> ORGANISM: Homo sapiens

<400> SEQUENCE: 16

Gly Arg Val Thr Gly Trp Gly Asn Leu Lys
1               5                   10

<210> SEQ ID NO 17
<211> LENGTH: 9
<212> TYPE: PRT
<213> ORGANISM: Homo sapiens

<400> SEQUENCE: 17

Glu Thr Trp Thr Ala Asn Val Gly Lys
1               5

<210> SEQ ID NO 18
<211> LENGTH: 20
<212> TYPE: PRT
<213> ORGANISM: Homo sapiens

<400> SEQUENCE: 18

Gly Gln Pro Ser Val Leu Gln Val Val Asn Leu Pro Ile Val Glu Arg
1               5                   10                  15

Pro Val Cys Lys
            20

<210> SEQ ID NO 19
<211> LENGTH: 22
<212> TYPE: PRT
<213> ORGANISM: Homo sapiens
```

<400> SEQUENCE: 19

Asp Ser Thr Arg Ile Arg Ile Thr Asp Asn Met Phe Cys Ala Gly Tyr
1               5                   10                  15

Lys Pro Asp Glu Gly Lys
            20

<210> SEQ ID NO 20
<211> LENGTH: 16
<212> TYPE: PRT
<213> ORGANISM: Homo sapiens

<400> SEQUENCE: 20

Arg Gly Asp Ala Cys Glu Gly Asp Ser Gly Gly Pro Phe Val Met Lys
1               5                   10                  15

<210> SEQ ID NO 21
<211> LENGTH: 24
<212> TYPE: PRT
<213> ORGANISM: Homo sapiens

<400> SEQUENCE: 21

Ser Pro Phe Asn Asn Arg Trp Tyr Gln Met Gly Ile Val Ser Trp Gly
1               5                   10                  15

Glu Gly Cys Asp Arg Asp Gly Lys
            20

<210> SEQ ID NO 22
<211> LENGTH: 11
<212> TYPE: PRT
<213> ORGANISM: Homo sapiens

<400> SEQUENCE: 22

Tyr Gly Phe Tyr Thr His Val Phe Arg Leu Lys
1               5                   10

<210> SEQ ID NO 23
<211> LENGTH: 5
<212> TYPE: PRT
<213> ORGANISM: Homo sapiens

<400> SEQUENCE: 23

Lys Trp Ile Gln Lys
1               5

<210> SEQ ID NO 24
<211> LENGTH: 4
<212> TYPE: PRT
<213> ORGANISM: Homo sapiens

<400> SEQUENCE: 24

Trp Ile Gln Lys
1

<210> SEQ ID NO 25
<211> LENGTH: 7
<212> TYPE: PRT
<213> ORGANISM: Homo sapiens

<400> SEQUENCE: 25

Val Ile Asp Gln Phe Gly Glu
1               5